United States Patent
Fletcher et al.

(10) Patent No.: US 11,129,532 B2
(45) Date of Patent: Sep. 28, 2021

(54) RETINAL CELLSCOPE APPARATUS

(71) Applicant: THE REGENTS OF THE UNIVERSITY OF CALIFORNIA, Oakland, CA (US)

(72) Inventors: Daniel Fletcher, Berkeley, CA (US); Robi Maamari, St. Louis, MO (US); Neil Switz, Oakland, CA (US); Todd Margolis, Kentfield, CA (US); Frank Myers, III, Oakland, CA (US); Kim Tyson, Ann Arbor, MI (US); Clay Reber, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 443 days.

(21) Appl. No.: 16/155,449

(22) Filed: Oct. 9, 2018

(65) Prior Publication Data
US 2019/0117064 A1    Apr. 25, 2019

Related U.S. Application Data

(63) Continuation of application No. PCT/US2017/027572, filed on Apr. 14, 2017.
(Continued)

(51) Int. Cl.
*A61B 3/13* (2006.01)
*A61B 3/12* (2006.01)
(Continued)

(52) U.S. Cl.
CPC .............. *A61B 3/13* (2013.01); *A61B 3/005* (2013.01); *A61B 3/0025* (2013.01);
(Continued)

(58) Field of Classification Search
CPC .... A61B 3/13; A61B 3/12; A61B 3/10; A61B 3/0025; A61B 3/005; A61B 3/0058;
(Continued)

(56) References Cited

U.S. PATENT DOCUMENTS

| 5,406,342 A | 4/1995 | Jongsma |
| 10,542,885 B2 * | 1/2020 | Fletcher .................. A61B 3/10 |

(Continued)

FOREIGN PATENT DOCUMENTS

| WO | 2015054672 A1 | 4/2015 |
| WO | 2017180965 A1 | 10/2017 |

OTHER PUBLICATIONS

ISA/KR, Korean Intellectual Property Office (KIPO), International Search Report and Written Opinion dated Apr. 14, 2017, related PCT international application No. PCT/US2017/027572, pp. 1-13, claims searched, pp. 14-19.
(Continued)

*Primary Examiner* — Mohammed A Hasan
(74) *Attorney, Agent, or Firm* — O'Banion & Ritchey LLP; John P. O'Banion

(57) ABSTRACT

A portable retinal imaging device for imaging the fundus of the eye. The device includes an ocular imaging device containing ocular lensing and filters, a fixation display, and a light source, and is configured for coupling to a mobile device containing a camera, display, and application programming for controlling retinal imaging. The light source is configured for generating a sustained low intensity light (e.g., IR wavelength) during preview, followed by a light flash during image capture. The ocular imaging device works in concert with application programming on the mobile device to control subject gaze through using a fixation target when capturing retinal imaging on the mobile
(Continued)

device, which are then stitched together using imaging processing into an image having a larger field of view.

43 Claims, 15 Drawing Sheets

Related U.S. Application Data

(60) Provisional application No. 62/323,542, filed on Apr. 15, 2016.

(51) Int. Cl.
| | |
|---|---|
| *A61B 3/10* | (2006.01) |
| *H04N 5/232* | (2006.01) |
| *A61B 3/00* | (2006.01) |
| *A61B 3/14* | (2006.01) |
| *G06T 7/00* | (2017.01) |
| *H04N 5/235* | (2006.01) |
| *H04N 5/33* | (2006.01) |
| *H04M 1/72409* | (2021.01) |

(52) U.S. Cl.
CPC .......... *A61B 3/0058* (2013.01); *A61B 3/0091* (2013.01); *A61B 3/10* (2013.01); *A61B 3/12* (2013.01); *A61B 3/145* (2013.01); *G06T 7/0012* (2013.01); *H04N 5/2354* (2013.01); *H04N 5/23222* (2013.01); *H04N 5/232935* (2018.08); *H04N 5/33* (2013.01); *A61B 2560/0431* (2013.01); *G06T 2207/10048* (2013.01); *G06T 2207/30041* (2013.01); *H04M 1/72409* (2021.01)

(58) Field of Classification Search
CPC .................. A61B 3/0091; A61B 3/145; A61B 2560/0431; H04N 5/232935; H04N 5/23222; H04N 5/2354; H04N 5/33; G06T 7/0012; G06T 2207/10048; G06T 2207/30041; H04M 1/72409
See application file for complete search history.

(56) References Cited

U.S. PATENT DOCUMENTS

| | | |
|---|---|---|
| 2003/0156258 A1 | 8/2003 | Tanassi |
| 2005/0041207 A1 | 2/2005 | Miller |
| 2005/0270484 A1 | 12/2005 | Maeda |
| 2008/0002152 A1 | 1/2008 | Collins |
| 2011/0279776 A1 | 11/2011 | Spaide |
| 2012/0050672 A1 | 3/2012 | Aikawa |
| 2012/0229617 A1 | 9/2012 | Yates |
| 2013/0135584 A1 | 5/2013 | Alasaarela |
| 2015/0002817 A1* | 1/2015 | Alasaarela ............... A61B 3/12 351/208 |
| 2015/0335239 A1* | 11/2015 | MacFougall ........... A61B 3/145 351/210 |

OTHER PUBLICATIONS

ISA/KR, Korean Intellectual Property Office (KIPO), International Search Report and Written Opinion dated Jan. 22, 2015, related PCT international application No. PCT/US2014/060184, pp. 1-13, claims searched, pp. 14-18.

* cited by examiner

RETINAL CELLSCOPE APPARATUS

CROSS-REFERENCE TO RELATED APPLICATIONS

This application claims priority to, and is a 35 U.S.C. § 111(a) continuation of, PCT international application number PCT/US2017/027572 filed on Apr. 14, 2017, incorporated herein by reference in its entirety, which claims priority to, and the benefit of, U.S. provisional patent application Ser. No. 62/323,542 filed on Apr. 15, 2016, incorporated herein by reference in its entirety. Priority is claimed to each of the foregoing applications.

The above-referenced PCT international application was published as PCT International Publication No. WO 2017/180965 A1 on Oct. 19, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to widefield imaging of the retina, and more particularly to a portable handheld smart phone-based retinal camera with eye guidance that is capable of capturing high-quality fundus images.

2. Background Discussion

Early diagnosis and frequent observation of a patients' ocular health can in many cases prevent vision loss. Toward that goal, healthcare systems are striving to improve outcomes by increasing the frequency of eye exams. To enable these efforts, interest is increasing toward making medical equipment more accessible while reducing costs. Recently, advances in smartphones with high quality cameras, large screens, internet connectivity, and low power consumption have reduced hardware costs and enabled a new type of less expensive, more portable ophthalmoscope.

Considering the physiology of vision, light is received and passes through the cornea at the front of the eye to the lens and is focused onto the retina in the back of the eye. The retina is a vascularized tissue responsible for transducing light imaged through the cornea, lens, and iris of the eye into a neural signal. Direct observation of the retina is important for diagnosing many diseases associated with vision loss. To arrive at a proper diagnosis, a device is required that sufficiently illuminates the retina and magnifies the image to provide improved detail of small structures within the retina.

Digital ophthalmoscopes image the retina in the posterior of the eye in a manner that allows for easy storage and transfer of the images. This advance allows for more efficient healthcare delivery by enabling medical assistants to take retinal photos and specialists to quickly interpret the results. The specialist and photographer need not be in the same location or work synchronously.

Existing ophthalmic equipment is typically designed for the use of trained experts. These products are produced with high quality optics and rigid tabletop-based assemblies to hold the system components in proper alignment. Imaging results are very good when the system is used by an operator who has invested substantial time to learn the intricacies of the device to take high resolution photos. However, the equipment is also very expensive and can pose a significant difficulty for new users to operate. In addition, patients must be upright and seated, which is often impractical especially among the sick and immobilized.

Increasing the accessibility and portability of retinal examination can improve the reach of ophthalmic care, in both inpatient and outpatient settings. However, optical performance typically suffers in portable devices, and especially handheld devices. These portable, low-cost, devices are generally subject to poor image quality due to lower mechanical rigidity of components, lower-cost (and quality) optics, and especially relative motion of the patient and imaging device due to lack of firm constraint of the position of the patient's head as is possible with table-top devices. These issues, particularly relative motion, typically require the pupils to be dilated in order to achieve imaging of sufficient quality and resolution, and images produced by these devices have a small field of view, poor image contrast and thus limited diagnostic utility.

Accordingly a need exists for a low-cost, portable, retinal imaging method and apparatus which overcomes the shortcomings of prior systems. The present disclosure meets that need and provides additional improvements directed at increasing ophthalmic care.

BRIEF SUMMARY

To perform screening and diagnosis of a wide range of retinal diseases requires high-quality, wide-field images of the retina. Handheld retinal cameras offer the potential to increase access to retinal imaging, due to their portability, as well as reduced cost compared to conventional instruments. However, the quality and reliability of portable and handheld intraocular imaging techniques is highly subject to factors including inexperience of the operator, motion of the imaging apparatus, and motion of the subject. Additionally, the field-of-view of portable fundus imaging technology is generally limited, posing a significant challenge for diagnosis in many retinal conditions. The disclosed technology provides an apparatus and method for digital ocular imaging with a mobile device-based retinal camera that leverages the compact size, high-resolution camera, large data storage capacity, wireless data transfer capabilities, and processing capability of current mobile devices to enable diagnostic retinal imaging. Embodiments of the technology are described which enable imaging through the pupil in a fashion allowing for machine-automated, or guided optimization, and increased intraocular field-of-view. The present disclosure improves the quality and reliability of point-of-care retinal imaging especially by less experienced operators.

In various embodiments, a handheld retinal imaging device, including lenses, illumination sources, and/or other optical elements connects to a mobile phone or portable computer running a mobile phone operating system, and is used for image capture, processing, storage, and/or data transmission. The device allows a completely portable and inexpensive system for retinal imaging. The handheld devices may be used in hospitals, clinics, and in the field to examine patients outside of the typical ophthalmology setting. For example, primary care or emergency room physicians can use the device to image the eyes of a patient and wirelessly transmit the images for remote evaluation.

At least one embodiment utilizes a fixation screen to guide the gaze of the subject's eyes, and thereby control the relative orientation of the optical system to various regions of the retina. This fixation guidance can be controlled in pre-programmed patterns, by operator input, and/or computational processing of preceding images to provide feedback-driven positioning of the fixation target. Various regions of the retina may be compiled to produce a large composite view of the retina by the imaging unit programming.

One embodiment of the present disclosure employs computational recognition of retinal anatomic structure, including but not limited to the optic disc and retinal blood vessels, to allow correlation of retinal location and position of the fixation target. In one embodiment, imaging system programming recognizes retinal structures and employs automated repositioning of the fixation target image adjacent regions of the retina. In another embodiment, image system programming recognizes retinal structures to provide overlays, or annotation, from prior imaging results, thereby assisting in the localization of regions of interest. In another embodiment, imaging device programming utilizes information from additional environmental sensors, for example accelerometers, inertial sensors, gyroscopes, pose sensors, and/or compasses to provide image orientation information during image acquisition and to assist in software-mediated alignment of image composites. This process may also be performed in real-time, wherein image unit programming continually guides the fixation target and constructs a growing composite and wide-field image of the retina.

In at least one embodiment, imaging device programming may control autofocus or capture serial images at varying depths of focus to provide three-dimensional image data not otherwise available from static images of the retina. In at least one embodiment, the process helps to simplify rapid and optimal focus of the retina. In at least one other embodiment, three-dimensional structures outside the primary retinal image plane may be imaged and dynamically reviewed, such as a video. This approach may be applied with, but is not limited to, retinal tears or detachments that lift away from the plane of the attached retina, excavation of the optic nerve, and presence of vitreal debris.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

1. Introduction

The disclosed Retinal CellScope device couples additional hardware to the application platform of a mobile device. Smartphones, tablets, or other similar mobile devices are particularly well-suited for use with the present disclosure, as they contain an imaging device (camera) along with program execution and data storage, and are typically capable of wireless as well as Bluetooth communication through existing telecommunication networks and devices. Although a remote communications capability is preferred, it is not essential and the acquired images can be stored in the device on permanent or removable media and accessed at a later time for evaluation.

2. Hardware Embodiments

Figure 1:
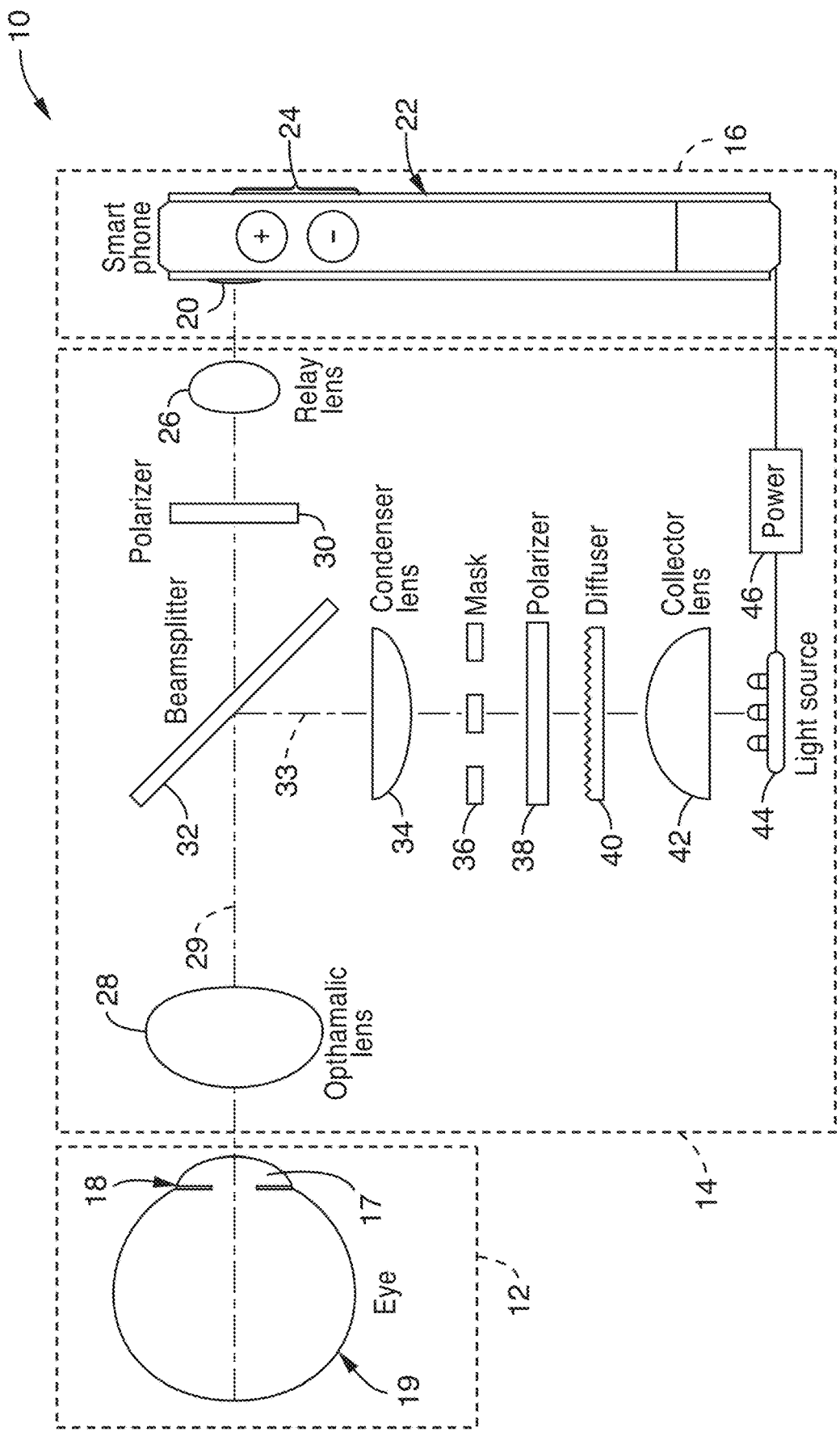
FIG. 1 is a block diagram of a retinal imaging system (Retinal CellScope) according to an embodiment of the present disclosure.

FIG. 1 illustrates an example embodiment 10 of an optical system 14 configured for coupling to a camera equipped mobile device 16 to capture images of a subject eye 12, and more specifically images through pupil 18 behind cornea 17 to obtain retinal 19 images. It will be appreciated that the camera feature of mobile device 16 has a camera lens 20 and display 22 that permits an initial visualization (e.g., preview mode) of views presented through the camera lens. Specific images can be obtained by activating a user input (e.g., pressing a button) 24 somewhere on the mobile device, or registering user inputs (e.g., gesturing captured by a touch screen) on device display 22, or otherwise entering user commands, including use of verbal command triggering (e.g., through the microphone of smart phone 16 utilizing voice recognition programming), or automated capture in response to application programming of the instant application determining that proper focusing has been achieved on the subject.

To properly view the eye of the test subject, optical system 14 augments the optical capabilities of mobile device 16. A coordinated pair of lenses, or groups of lenses, work interoperably to provide an objective lens. In the example embodiment 10, lens 20 of the mobile device 16 is aligned with a relay lens 26 and an ophthalmic lens 28 illustrated being along an optical path 29 depicted with a horizontal dashed line (from camera through lensing to the patient's eye) in order to visualize and image the retina and other eye structures.

The relay lens 26 and ophthalmic lens 28 are preferably mounted at a distance equal to the sum of the focal lengths of lens 26 and lens 28 from each other, with these lenses comprising either single lenses or multiple lenses which are proximal one another, mechanically coupled, or even cemented together. The relay lens 26 and the ophthalmic lens 28, or similarly positioned compound lenses, utilized in at least one embodiment of the present disclosure can produce a field-of-view that is greater than a direct ophthalmoscope, and equivalent or greater than the standard tabletop ophthalmoscope.

The selection of dimensions for relay lens 26 will be influenced by ophthalmic lens 28 as well as the optical characteristics and capabilities of the mobile phone or camera. The larger the focal length of the relay lens, the less magnification is provided of the image of the retina onto the sensor of the camera. Therefore, the lens characteristics are preferably selected to capture the full field of view generated by the ophthalmic lens so that it is circumscribed onto the sensor of the camera. However, alternative configurations can be selected where the smaller focal length of the relay lens would create higher magnification of the retina in other embodiments.

For example, in one embodiment, relay lens 26 preferably comprises an achromatic lens with a 12.5 mm diameter and a 20 mm focal length that consists of two optical components made up of S-BaH11/N-SF10 substrate cemented together to form an achromatic doublet. By way of example and not limitation, the ophthalmic lens 28 preferably comprises a 54 diopter double-aspheric lens configured for use in indirect ophthalmoscopy with the slit lamp.

To minimize reflections within the system, at least one optional polarizer may be incorporated (e.g., 30, 38). In the example shown, one polarizer 30 is placed in the illumination path, and a second polarizer 38 may be placed crossways to the first polarizer and imaging path, in an illumination path 33.

A beam splitter 32 is positioned at a sufficient angle (e.g., typically a 45-degree angle) in relation to imaging path 29. The beam splitter forms an intersection between imaging path 29 and illumination path 33. The beam splitter reflect light received from an illumination path 33 and directs this by the beam splitter along a portion of imaging path 29 towards the eye 12 of the subject. It should also be recognized that any of the described optical elements may be combined without departing from the teachings of the present disclosure; for example combining polarizer 30 with beamsplitter 32, by using a polarizing beamsplitter.

In the embodiment shown in FIG. 1, the eye 12 is illuminated with a light source 44 driven from a source of electrical power 46 (e.g., a separate battery source, power from the camera, solar power, so forth and combinations thereof) that is preferentially reflected from beam splitter 32 to ophthalmic lens 28. It should be appreciated that light source 44 is preferably configured to produce light at selected wavelengths and intensities. For example, the light source can be made from one or more light-emitting diodes or other light sources and the light source may also use fiber optic cables to deliver light. The light sources (e.g., LEDs) can also comprise white, red, infrared, blue, green, or any combination of colors. Light source 44 may alternatively comprise or incorporate monochromatic lights in any combination of colors or patterns. Light source 44 can also be controlled, either through circuitry within optical system 14 (not depicted in this embodiment), or more preferably through a wired, or more preferably wireless, communication connection with mobile device 16, such as through Bluetooth or Wi-Fi capabilities of the mobile device.

Light source 44 preferably has one or more light emitters that can be individually controlled, with its light output being collected by collection lens 42, such as located at a distance approximately equal to the focal length of lens 42. A diffuser 40 is located along this illumination path 33 to receive the condensed beam exiting collecting lens 42. Diffuser 40 may comprise one or more optical devices configured to sufficiently, and evenly, diffuse the light. The diffuser, for example may comprise ground glass, plastic, or any other substrate, or combination of substrates, that will allow for near-uniform illumination. The diffuser ensures that the light emissions from high intensity light sources are not directly imaged onto the retina.

Polarizer 38 is placed in illumination path 33 after diffuser 40, and preferably positioned so that the polarization of the illumination light that is ultimately incident on the beam splitter 32 is in s-polarization. Light transmitted through polarizer 38 is directed through a mask 36 that can be of any desired configuration, insofar as it sufficiently allows selectively controlling light transmission through areas of the illumination path 33. Use of a programmable mask (e.g., LCD, optical shutter array, etc.) in mask 36, allows directing any desired pattern of light onto the cornea of the eye 12 of the subject. In another embodiment, the mask and polarizer positions may be reversed. Patterned light from the masking step is then condensed through a condenser lens 34, still along illumination path 33. Light emerging from the condenser lens 34 is directed to one face of beam splitter 32.

Beam splitter 32 is mounted at an angle such that the illumination reflecting off of it from illumination path 33 is directed through ophthalmic lens 28 to eye 12. The combination of collector lens 42, condenser lens 34, and lens 28, and the relative spacing between components are chosen such that the pattern of mask 36 is imaged onto or near the cornea 17 of eye 12.

After traversing the cornea, the illumination received through lens 28 travels to the anterior chamber of eye 12, that is to say it travels through the dilated pupil, the lens of the eye, and the vitreous humour to the retina. The image of mask 36 is chosen to be in focus at the cornea and having dimensions that allow the illumination to pass through a peripheral region of the cornea and pupil into the vitreous humour to illuminate the retina.

In one embodiment, the retina is illuminated using a cone of light that enters the dilated eye at the periphery of the pupil to provide illumination, while imaging through the center of the pupil to additionally avoid pollution of the collected image with illumination light reflected, e.g., off the corneal surface.

Although the pupil of the subject is typically dilated, this is an optional step. In at least one embodiment, apparatus programming is configured for automatically assembling multiple images of the retina captured by directing the gaze of the eye with fixation lights described below, so that imaging can be performed even without dilation of the subject's pupil.

By imaging the illuminated mask pattern on the cornea, reflections off of the corneal and other surfaces that would otherwise corrupt the image of the retina are reduced. Different mask designs can be inserted to avoid reflections in different locations, such that a series of images of the retina could be collected and combined to create a single reflection-free image. For example, a set of masks within the optical system can be automatically or manually iterated to collect images with and without reflections in different parts of the image, so that the images can be combined to create one image with minimized reflections.

Furthermore, the image of the annulus of light is focused on the cornea and defocuses as it approaches the retina so that a uniform illumination onto the retina is created. The annulus needs to be focused sufficiently to penetrate the cornea, anterior compartment, and lens while in focus, but defocused by the time it gets to the retina so that the illumination of the retina is uniform. The depth of focus of the illuminated annulus is determined by the numerical aperture (NA). Preferred numerical aperture values are selected from the group consisting of less than or equal to 0.01; less than or equal to 0.1; less than or equal to 0.25; less than or equal to 0.5; and less than or equal to 1.

The retina of the subject acts as a surface that depolarizes the incoming light. The depolarized light reflecting off of the retina then returns through the ophthalmic or objective lens 28.

The returning reflected light through lens 28 is directed to beam splitter 32. Beam splitter 32 is configured so that the rays in the P-polarization state are preferentially transmitted through the beam splitter along the imaging path 29 shown in FIG. 1. The transmitted light through the beam splitter then travels through imaging polarizer 30 that is positioned in the P-polarization state relative to the beam splitter 32. These rays then travel through lens 20 to the camera of mobile device 16. Any light that does not pass through the beam splitter may be collected in an optional light trap, for instance made from matte black paint, which can be painted on the interior housing surfaces behind the beam splitter to reduce reflection off the surfaces. The light trap can be configured using any known or desired technique, including but not limited to the use of felt, matte, conical design, flat black paint to minimize reflection of illumination light back to the image detector.

The rejection of light in the imaging path that is of the same polarization state as the illumination by the system is important because it acts as a method of reducing the artifacts created by reflections off of surfaces in the system. For example, light in the S-polarization state will reflect off of component surfaces including both sides of ophthalmic lens 28, the cornea, the relay lens 26, as well as any other surface where there is a change in the index of refraction. Since P-polarization relative to the beam splitter is preferentially transmitted through the beam splitter and/or subsequent optics in the imaging path, reflective artifacts in the S-polarization state off of the interfaces in the imaging path are reduced in the final image. The depolarization that occurs at the retina allows an image to be collected that is comprised mainly of rays in the P-polarization state relative to the beam splitter surface.

The properties of beam splitter 32 are such that it preferentially reflects light that is polarized parallel to its vertical axis (e.g., path 33), and transmits light that is polarized parallel to its horizontal axis (e.g., path 29). This allows vertically polarized light to be reflected towards the ophthalmic/objective lens 28 which then forms an image of the mask near pupil 18. The light passes through the pupil 18 and illuminates retina 19. As the light reflects off the retinal surface, it is depolarized, creating light in both the vertical and horizontal axes relative to beam splitter 32. Depolarized light then passes through pupil 18, ophthalmic/objective lens 28 to beam splitter 32. Light that is parallel to the horizontal axis of the beam splitter 32 is preferentially transmitted through beam splitter 32 towards portable device 16. The polarized light then travels through polarizer 30 on optical path 29 (parallel to horizontal axis of beam splitter 32 and perpendicular to polarizer 38), through relay lens 26 and into lens 20 of mobile device 16. This cross-polarization technique is important for limiting reflection artifacts from the objective lens 28 and surface of the eye 12.

It should also be noted that the imaging light path 29 and the illumination light path 33, overlap from the beam splitter 32 to retina 19. The illumination light path is directed from beam splitter 32 towards retina 19, and the light that reflects off retina 19 reaches objective lens 28 and then beam splitter 32 is part of the imaging light path towards the camera of the mobile device 16.

The imaging system shown in FIG. 1 can also include optional optical filters such as color glass filters or any type of interference filter (bandpass, longpass, shortpass, other filters and combinations thereof) that are positioned within the imaging path. These filters can be additionally or alternatively contained in mobile device 16, or implemented through the use of image processing operations therein.

Images of the structures of eye 12 that are received by mobile device 16 can be processed, stored or transmitted to remote servers or computers for storage and evaluation. The system can be configured for wired or wireless transmission methods including Wi-Fi, Bluetooth, cellular networks, and Ethernet.

Figure 2:
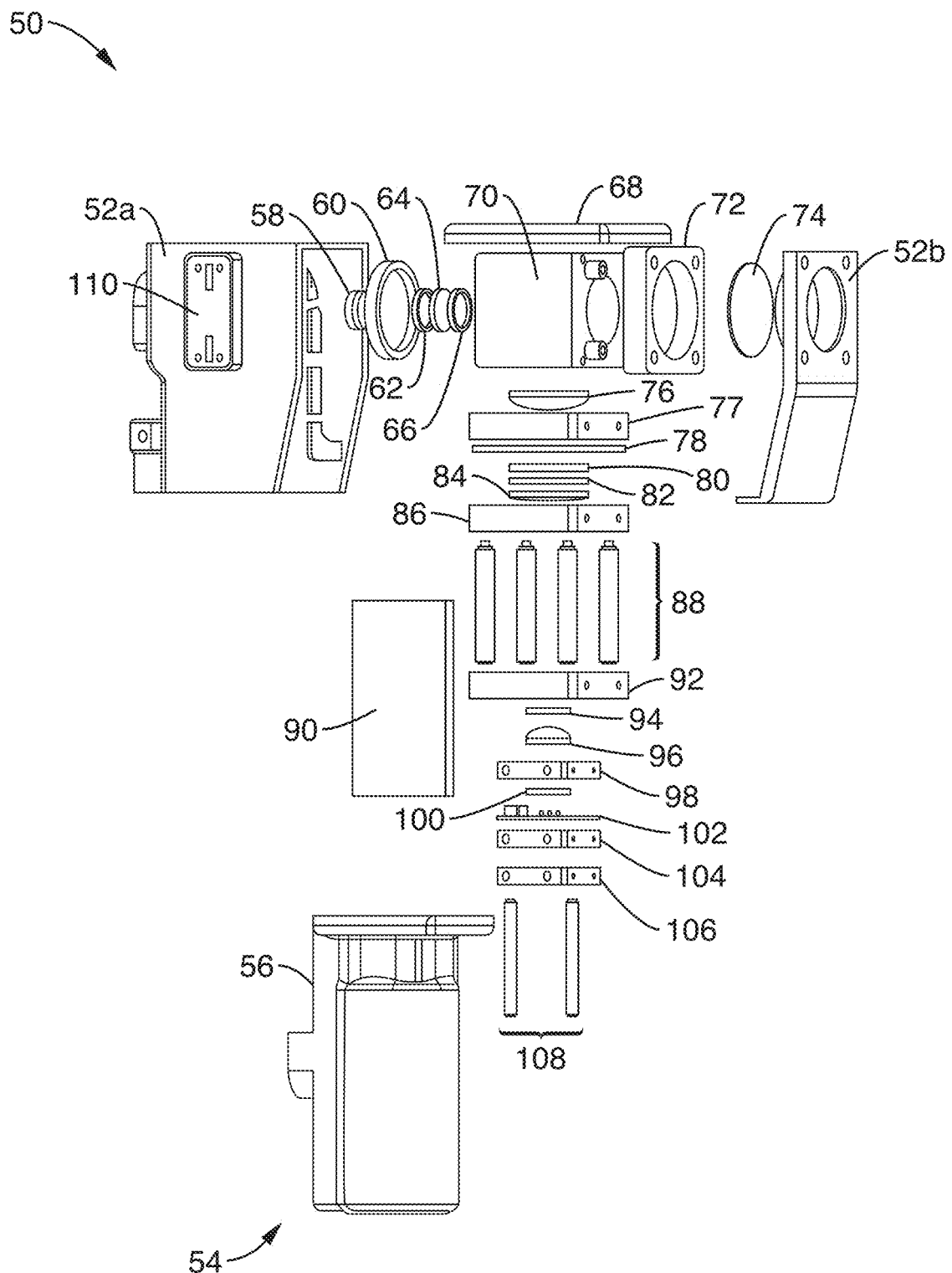
FIG. 2 is an exploded view of the retinal imaging system according to an embodiment of the present disclosure.

FIG. 2 is an example ocular device embodiment 50, shown schematically in FIG. 1, and depicted here in an exploded form so that the internal components can be viewed. A mobile device interface portion 54 of housing 52a has a slot 56 for receiving the mobile device 16 seen in FIG. 1.

In at least one preferred embodiment, the disclosed ocular device contains a coupling adaptor so that the lens system can be specifically built with a dedicated holder to align camera lens 20 of mobile device 16 of FIG. 1 with the optical axis of ocular device 50. In FIG. 2, the mobile device is optically coupled to the first relay lens 58 by sliding the mobile device into slot 56 of section 54 of ocular device housing 52*a*. Although a slot type configuration is preferred, other methods for coupling the mobile device with the device housing can be utilized without limitation, for example mechanically clipping the mobile device to the ocular device, or magnetically aligning the devices and the two optical axes, or other mechanism for retaining the lens of the mobile device in the proper position in relation to lens 58 of ocular device 50. The aligned axes of the housing optics and the mobile device provide a minimized image of the retina to be imaged onto the sensor of the mobile device camera.

Housing 52*a*, 52*b* may comprise any material, or materials, which are sturdy and sufficiently rigid for maintaining the alignment of the optics and to seal the optics from ambient light. For example, an acrylonitrile butadiene styrene (ABS) plastic, or similar, can provide a suitable material for the housing. However, the housing may be alternatively made from other materials including other plastics, metals, or a combination thereof.

Housing 52*a*, 52*b* houses relay lens 58, in the same optical path as a polarizer 64, held in place by retaining rings 62 and 66; retaining ring 60 also serves to connect the assembly to the beamsplitter 70 (beamsplitter cube). A cap 68 (e.g., plastic) is seen over the housing. The housing is also configured for retaining a battery, or batteries, 90.

A polarizing beam splitter 70 forms the junction between the imaging path (horizontal path in this figure) and the illumination path (vertical path in this figure). Continuing along the imaging path, output from beamsplitter 70 is coupled through an ophthalmic lens 74, positioned by spacer 72 into housing portion 52*b*.

Now the illumination section is detailed from the source of light back up to where it reaches beamsplitter 70. It will be noted that the housing retains (houses) the optical components that can be positioned using cage plates, or other retention mechanisms, configured for holding and mounting optical components. For instance, in one embodiment, cage plates accepting one inch optics can be used with coupling components that accept 0.5 inch components.

A connector 110 is shown, extending from housing 52*a*, or other section of ocular device 50 as desired, to which a fixation screen (described in a later section) is mechanically and electrically coupled to provide electrical signal (digital communication) and power connectivity.

From below the illumination source are shown a structure which is exemplified with a rail system extending through spacers and lens holders to retain them in proper alignment and distance from one another. In the lower section are seen rails 108 for inserting into separator plates 106, 104, and through light source 102, and through separator 98 which retains collector lens 96 between retaining rings 94 and 100 and couples to the upper portions starting at separator plate 92, which is separated from separator plate 86 by standoffs 88. A retaining ring 84 secures a diffuser 82, above which is polarizer 80, annular mask 78, and another separator plate 77 associated with condenser lens 76, the output if which is coupled to beam splitter cube 70.

The ophthalmic lens 74 in at least one embodiment of this disclosure is configured to be interchangeable, thus providing different levels of magnification in response to changing the lens. By way of example and not limitation, lens 74 can be retained in a plastic casing that is removable using a clipping system or a release button that enables an objective lens in the plastic housing to be removed when the clip or button are pressed. Another objective lens with a different power can then be attached to the housing and will remain stationary and fixed to the remainder of the ocular device. The preferred interchangeable front lenses have a diopter selected from the group consisting of a Diopter≥1; a Diopter≥5; a Diopter≥10; a Diopter≥15; a Diopter≥30; and a Diopter≥50.

Preferred imaging systems have objective lenses to capture a field-of-view (FOV) selected from the group consisting of FOV>5 degrees; FOV>10 degrees; FOV>20 degrees; FOV>25 degrees; FOV>30 degrees; FOV>45 degrees; FOV>55 degrees; and FOV>70 degrees.

In at least one example embodiment, the device housing contains a rechargeable battery, electronics, and illumination optics arranged in linear fashion along the illumination path within the handle of the device to enable single-handed operation, as described below.

FIG. 3A through FIG. 3D illustrates views of the ophthalmic device 50 of FIG. 2 shown coupled with a handheld mobile device (e.g., 16 shown in FIG. 1) with integrated camera (e.g., a smart phone). A fixation screen 130 is shown in this example embodiment on the right side of the housing, incorporating a display with simple 'fixation' graphic 132 to which the gaze of the subject can be directed. In addition, the housing is preferably configured with an eye cup 134 to block extraneous light from entering lens 74, while it aids in positioning and stabilizing of the device proximal the face of the subject. For example, the operator can hold the ocular device 50 up to the subject's eye so that the rubber cup 134 is held stationary on the subject's orbit. The distance between lens 74 of FIG. 2 and the surface of the subject's eye (cornea) is in a range that is near the appropriate working distance as specified by the lens manufacturer to allow imaging of the subject's retina. A working distance of approximately 10 mm to approximately 15 mm is typical.

Once the apparatus is generally positioned over the eye of the subject, the user can activate the light source and pre-view an image on the display 16 of the mobile device. It will be noted that the user operates the ocular device with the eyecup positioned over the eye of a subject; the subject and user are not the same person. Preview images allow the user (not the subject) to make small position adjustments and to focus the view before acquiring a final image. In FIG. 3D the subject is seen with their right eye following the fixation graphic 132, as indicated by the arrow on the dashed line from their eye to the focus point on the graphic. It will be appreciated that although it is the right eye which is fixated, the left eye track is parallel as also seen by the arrow on the other dashed line; thus providing an indirect mechanism for controlling the positioning the eye track of the eye being images. It should be appreciated that to image the other eye, fixation screen 130 is then connected on the alternate side of unit 50 and the subject repositioned. In at least one alternative embodiment, a separate fixation screen is mounted on each side of the unit, for example using a flip screen mechanism to deploy each of the screens.

The fixation screen 130 is used to direct subject gaze, and may comprise any of numerous forms of display elements. By way of example and not limitation, fixation screen 130 may comprise a light emitting, light transmitting, and/or light reflective screen that preferably provides a high-contrast output and is configured for software programmatic control. In particular, the screen may comprise separate discrete elements, or an array of display elements. These display elements may comprise LED, OLED, LCD screen, E-Ink, or other such addressable display technologies. In at least one embodiment at least one diffractive and/or refractive lens is placed in front of the screen to aid patient focus on the screen. In one embodiment fixation point can be directed to an imaging system through a prism; which allows a direct projection of the fixation point onto the eye that is being imaged.

Figures 3A, 3B, 3C:
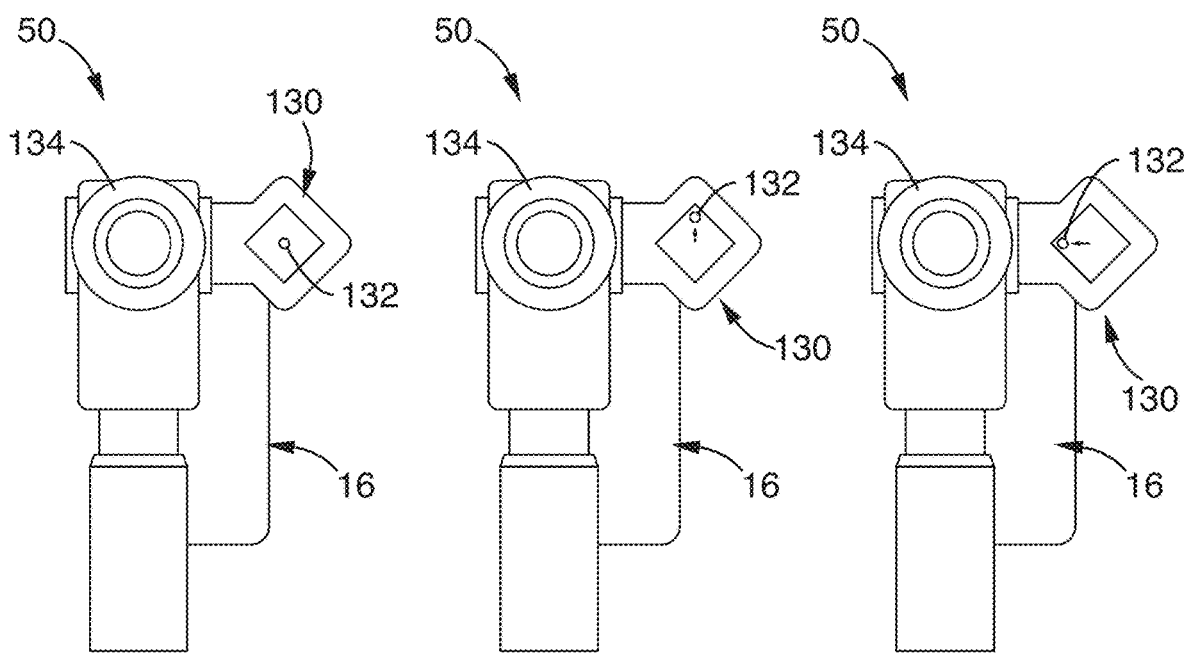
FIG. 3A through FIG. 3D are image renditions of the retinal imaging system according to an embodiment of the present disclosure, showing a fixation screen with fixation graphic.
Figure 3D:
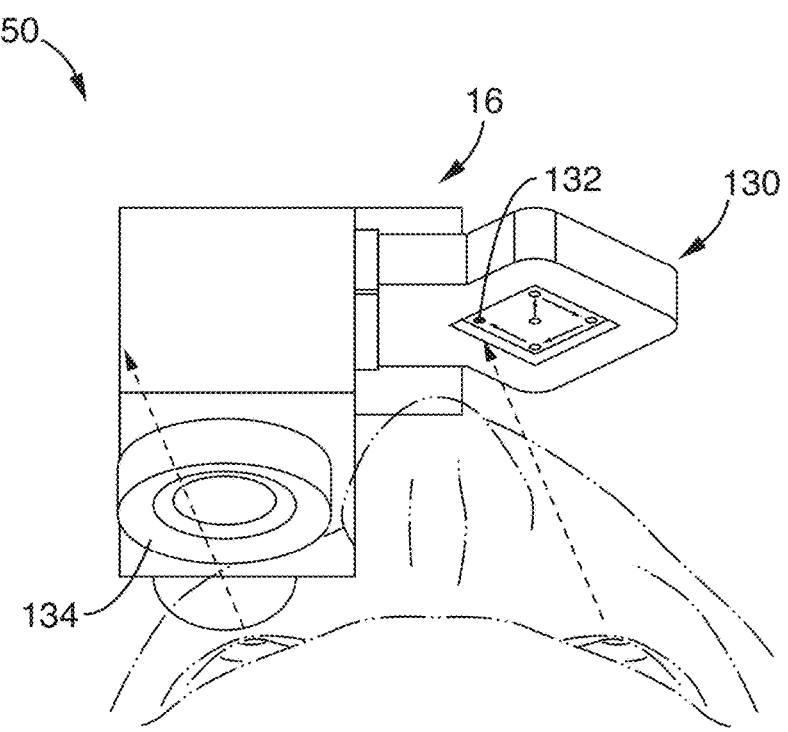

Returning to the fixation screen of FIG. 3A through FIG. 3D, the screen is designed to face the patient and be observed by the eye not under test. As a patient moves their gaze to center a foreground element in their field of view, the eye under test will also move. This is demonstrated in FIG. 3D, in which the subject being tested uses the right eye to follow the location of the fixation target 134 shown on the fixation screen to the left position, with the left eye moving to the corresponding position. In FIG. 3A a fixation target is seen to illicit a central gaze response, while in FIG. 3B the target is shown depicting a graph for upward gaze, and in FIG. 3C the target is shown displayed for a left gaze.

The fixation dot (e.g., green), such as shown on the screens in FIG. 3A through FIG. 3D, is in at least one embodiment, controlled by a microcontroller located within the housing of the Ocular CellScope to provide a fixation target for the contralateral eye. During fixation, the subject is directed towards a small area (e.g., 5-pixel diameter green dot) that is presented on the screen and to which the eye not being imaged is directed. As the subject redirects gaze when the fixation target is presented at various locations, corresponding regions of the retina of the eye being imaged can be captured. The fixation display is attached into the right slot (subject's view) when the left eye is being imaged in order to direct the eye movements of the right eye. These locations enable the user to capture a superior (B), inferior, nasal (C), temporal, and posterior pole fundus photo (A).

Figure 4:
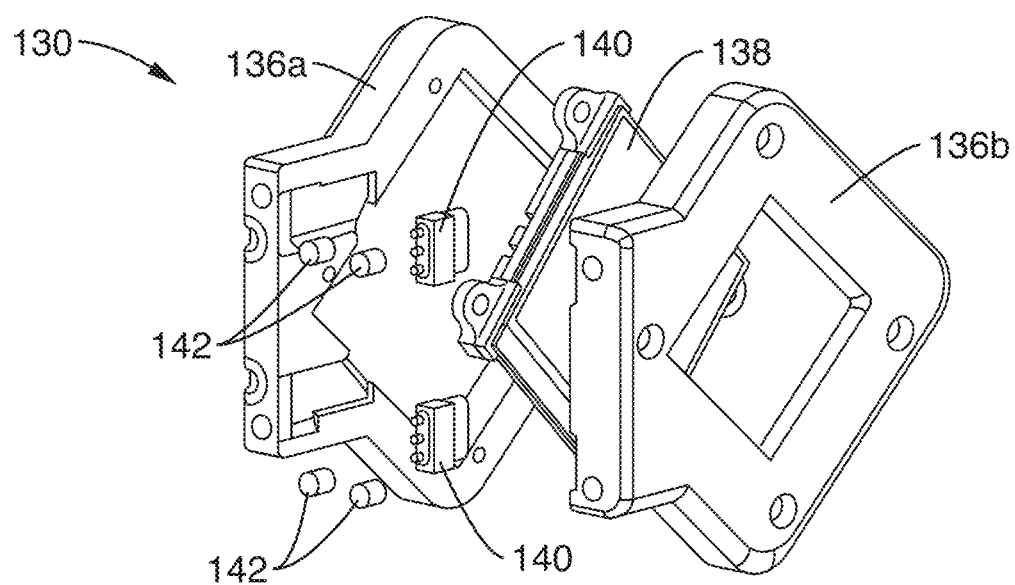
FIG. 4 is an exploded view of a fixation screen according to an embodiment of the present disclosure.

FIG. 4 depicts a fixation screen 130, with its housing 136a, 136b for retaining a display 138. The fixation screen can be mounted on the side of the device and held in place by magnetic or mechanical force. The attachment is designed, in this flexible arrangement, so that the screen can easily be placed on either side of the case to control the opposite eye while one eye is being imaged. The fixation screen is configured for receiving control signals from a control processor (from the ocular device coupled to the mobile device, or from the mobile device itself) either through a wired connection (when the fixation screen is attached) or through an RF protocol (such as, but not limited to, ZigBee, Bluetooth, or Bluetooth Low Energy). Connectors 140 are shown, and in one preferred embodiment utilize spring loaded pins to provide a convenient way to transmit power and focal point control data, while easily aligning the contacts without requiring extra force. In one embodiment, magnets 142 are used to attach the fixation screen to the ophthalmic device 50. Alternatively, any desired form of mechanical interconnection (e.g., pins, slots, notches, or other engagement and/or alignment mechanisms and combinations thereof) may be utilized without departing from the teachings of the present disclosure.

Figure 5:
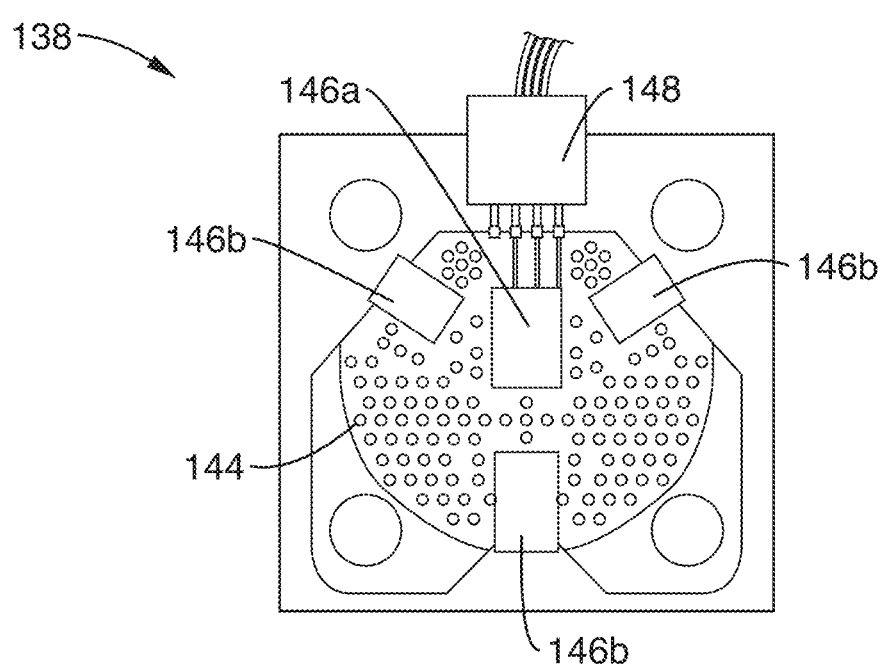
FIG. 5 is an image rendition of a simple fixation display screen according to an embodiment of the present disclosure.

FIG. 5 illustrates an example embodiment 138 of a very simple form of fixation screen utilized in a test embodiment. A prototyping printed circuit board (PCB) 144 is shown populated with a single display element 146a (e.g., white LED) at the center, and a ring of multiple display elements 146b (e.g., deep red LEDs) separated from the central display element by a desired radial distance, for example 3.15 mm in this prototype. These display elements are controlled by a controller circuit which communicates either wirelessly, or more preferably through a wired connection 148 back to the electronics in the main portion of the housing.

Figure 6:
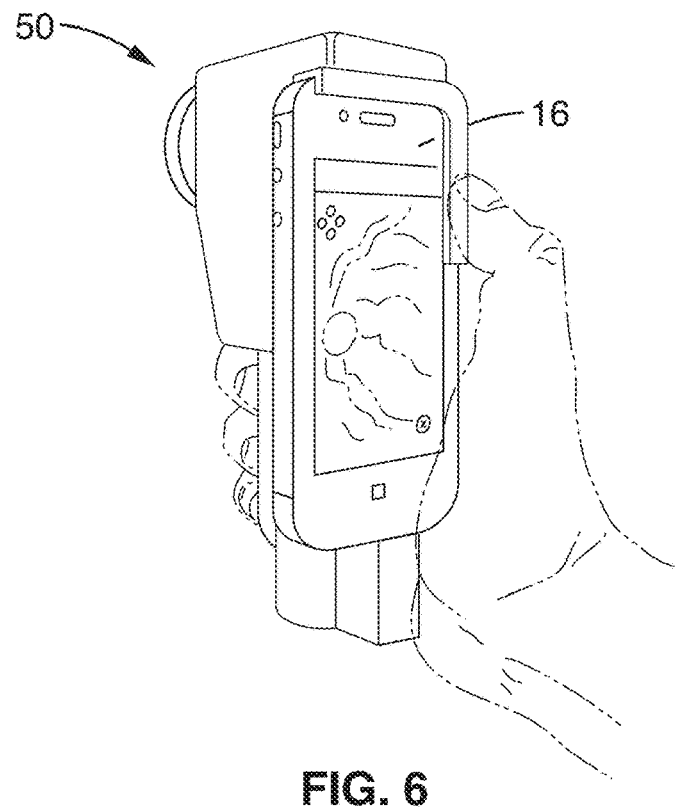
FIG. 6 is an image rendition of the retinal imaging system according to an embodiment of the present disclosure, shown in the hand of a user.

FIG. 6 illustrates an example embodiment of the combined ophthalmic device (Retinal CellScope) 50 coupled to the mobile device 16, shown in the hand of the user performing imaging (subject is not shown). The Retinal CellScope apparatus is designed so that the device housing contains a source of electrical power (e.g., rechargeable battery), electronics, and illumination optics for instance arranged in linear fashion along the optical axis within the handle of the device to enable single-handed operation. As shown, this enables the user to control the device using the thumb of the hand holding the device or any fingers in the other hand.

Figure 7:
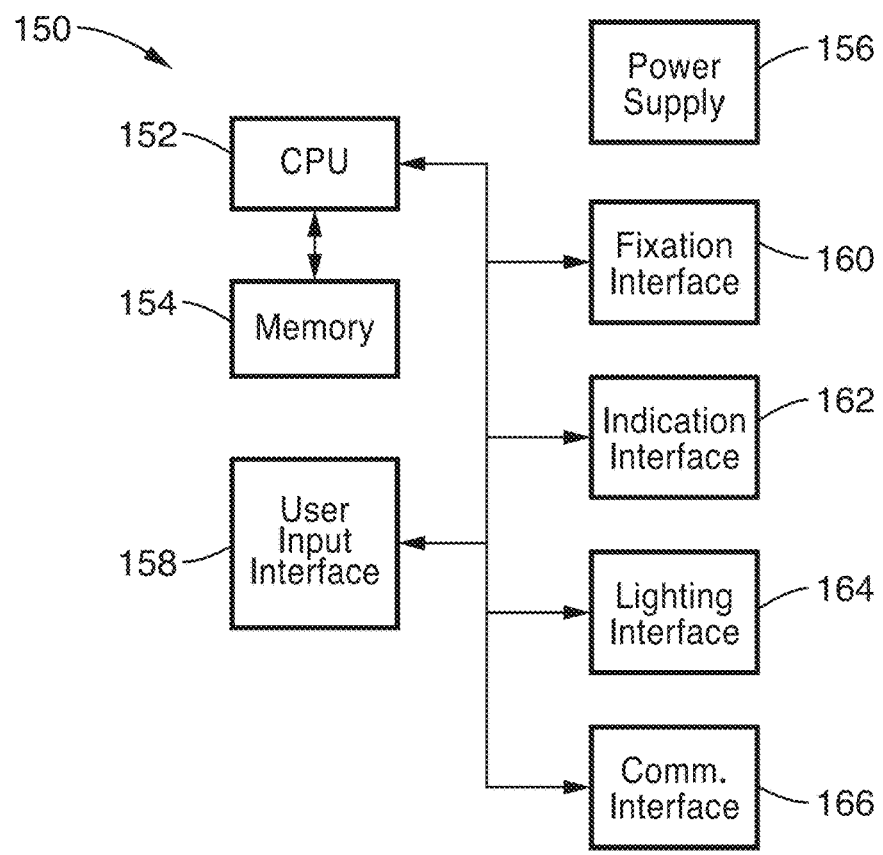
FIG. 7 is a block diagram of electronics for the retinal imaging system according to an embodiment of the present disclosure.

FIG. 7 illustrates a block diagram 150 of the electronics in the ophthalmic device (Retinal CellScope) as configured for coupling to a mobile device (e.g., smart phone). A controller circuit is shown comprising CPU 152 and memory 154 (one or more CPUs and memories without limitation), such as contained within one or more microcontrollers or similar programmatic circuits, is configured to control the operations of lighting and image capturing. The circuit is shown with a source of power 156 for powering these elements preferably without the need of drawing power from the mobile device. Coupled to the controller are shown a user input interface 158 configured for receiving specific selections from a user on the ophthalmic device, a fixation interface 160, indication interface 162 for generating indicators to a user on system state, a lighting interface 164 for controlling the lighting directed to the pupil of the subject, and a communications interface 166 configured for communicating with the mobile device and optionally to other devices. It should be appreciated that many specific operations of the apparatus, comprising the combination of ocular imaging device and mobile device, can be controlled by either the controller 152, or programming executing on the microprocessor of the mobile device and communicated to the ocular device, such as its controller.

3. Software

In addition to its camera feature, the ophthalmic device also makes use of the microprocessor on the mobile device for executing application programming of the present disclosure to control various aspects and components of the apparatus as well as to control the acquisition, processing, storage and transfer of images.

In one embodiment, the images that are acquired by the apparatus are simply transferred to a remote device for processing and storage.

The application programming (software) which is loaded on the mobile device preferably performs operations in five areas, comprising: (1) image acquisition; (2) image processing and storage; (3) control of illumination; (4) control of the fixation screen; and (5) external communications.

The image acquisition programming of the mobile device provides control over the device components in the production of the initial image. For example, in one embodiment, the mobile device programming controls the actuation timing, intensity, duration and wavelength of the components of the illumination path as well as focusing, aligning, previewing and final acquisition of the image. It should be appreciated that although the optical elements seen in FIG. 1 and FIG. 2 depict the use of fixed optical elements, embodiments of the present disclosure include the use of adjustable optical elements (e.g., lenses, filter, polarizers, diffusers, masks, and so forth) in which their relative positions (linearly and/or rotationally) and/or specific operation (e.g., focal length, diffusion extent or pattern, mask pattern, etc.) can be changed under program control to optimize image previewing and capture.

Preview images on the display of the mobile device allow the user to evaluate and change the location, illumination and focus of the apparatus before the final image is acquired, such as in response to using touchscreen commands on the attached mobile device. Therefore, the previews that are produced by the apparatus are preferably of sufficient detail and orientation to permit adjustments.

One characteristic of the system illustrated in FIG. 1 is that it creates a real, inverted image on the imaging sensor of the mobile device. Due to the inverted nature of the preview on display screen of the mobile device, proper positioning for adequate image acquisition is more difficult because movement to the left corresponds to a right shift on the screen, and movement down corresponds to an upward screen movement. This is similar to the inverted nature of the binocular indirect ophthalmoscope.

In at least one embodiment, the programming of the mobile device is modified to invert the image displayed on its display screen while displaying indicia, and reading touch inputs in their normal orientation, so that the images are shown in their proper orientation simplifying user control. By way of example and not limitation, the preferred transformation can be performed using a reflection across the horizontal and vertical axes. The use of the horizontal and vertical transformation can be performed by the dedicated camera application to create an upright representation of the object in the preview mode that is more intuitive for the user to operate.

There are many aspects of the light source (44 in FIG. 1) that can be controlled by the programming of the mobile device in those embodiments where the light source is not simply actuated by a power switch. Light source 44 can be actuated through a wired or wireless connection with the mobile device in conjunction with the mobile device battery or the power supply and circuit 46 shown schematically in FIG. 1. This enables the mobile device 16 to trigger light source 44 in synchrony with the capturing of the retinal image. Wireless control via Bluetooth or infrared of a single-board microcontroller can also be utilized to control the display elements (e.g., LEDs).

Figure 8:
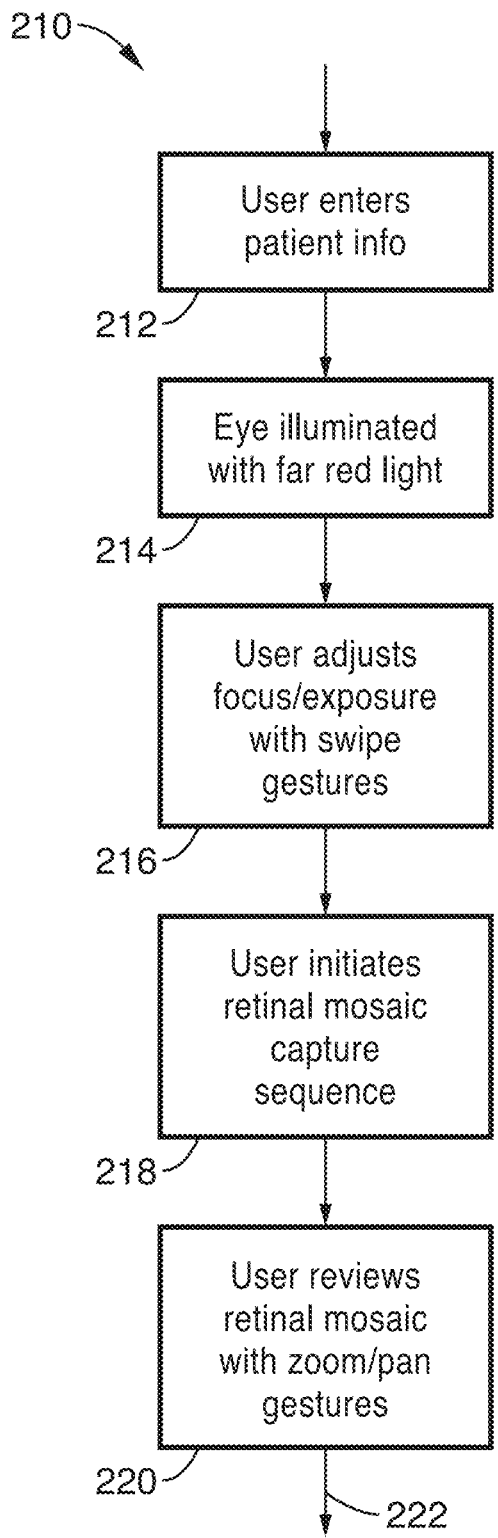
FIG. 8 is a flow diagram of user interaction in a retinal imaging system according to an embodiment of the present disclosure.

FIG. 8 illustrates an example embodiment 210 of user interactions with the ocular system. Interaction is exemplified as commencing with a user entering patient (subject) information 212. The ocular imaging then begins with the eye illuminated by a far red light 214 (e.g., a wavelength of light near or below human visible spectrum) during a preview mode, upon which the user adjusts 216 focus and/or exposure controls, such as with swipe gestures (touch screen selections/gestures). The user then initiates a retinal mosaic capture sequence 218, after which the captured mosaics can be reviewed 220 with zoom and pan gesture control, before being stored or transmitted 222 (or retaken as desired).

Thus, it will be appreciated that the workflow of the interface starts with the mobile device sending a signal to the microcontroller to turn on a low-level light or a light with an alternate wavelength when the dedicated camera application is initiated on the mobile device. Once the operator obtains the desired focus and field-of-view, a second signal can be sent to the microcontroller by a number of methods including but not limited to pressing a button on the device, verbal command recognized by device programming, or automatically triggered when the image is brought into focus. This second signal can trigger a second light source to turn on or flash when the image is being captured. This is beneficial because it allows a low-level light and/or alternative wavelength light to be used for focusing on the retina and a (potentially separate) high intensity light flash that can be used to capture the final image, thus minimizing the light exposure to the subject's retina.

Figure 9:
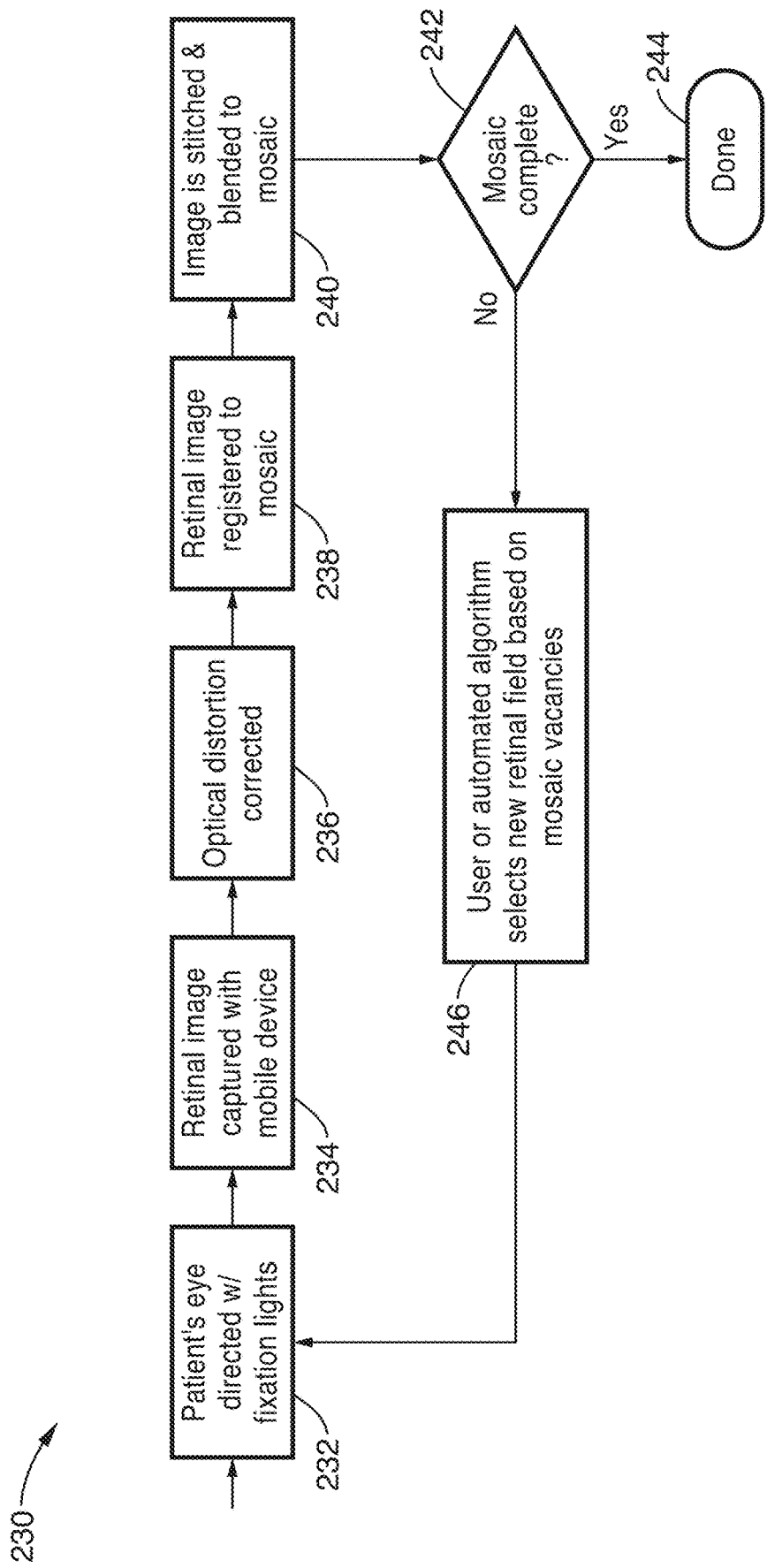
FIG. 9 is a flow diagram of a retinal mosaic capture sequence in a retinal imaging system according to an embodiment of the present disclosure.

FIG. 9 illustrates an example embodiment 230 of a retinal mosaic capture sequence. When this phase is reached, as was seen in FIG. 8, then patient's eye is directed 232 in a desired direction utilizing fixation lights (controller outputs a control signal, or pattern, to the fixation display). Retinal image is captured 234 with the mobile device under control of application programming for the present disclosure. Optical distortion is then corrected 236, and the retinal image is registered 238 to fill the respective element of the mosaic, after which elements of the mosaic are stitched together into a complete mosaic image 240. A check is made 242 if the mosaic is complete. If the mosaic is complete, then processing is completed 244, otherwise block 246 is executed to select a new retinal field based on missing areas found in the mosaic, after which execution returns to step 232.

Thus, it has been seen above that mobile device software programming is also configured to control the sequence and duration of light source actuations to produce temporal and spatial illumination of the eye. The ocular imaging system can then capture images of different fields of the retina and then process and compile the images (mosaic elements) and stitch them together to show the entire field of the retina as one image. The elements comprising the light source may be in the "on" or "off" state in various combinations and can be activated to produce images that highlight the details of the different regions of the retina to increase resolution.

The wavelengths of the light source elements can also be matched to either or both of the absorption or reflectance of different components of the fundus including melanin, macular pigment, the optic disc, oxygenated blood, and deoxygenated blood. The light wavelengths of the light source can also be in the scotopic and photopic response range of the eye.

However, the system can also use light sources (e.g., LEDs) that emit outside of the scotopic and photopic response region of the eye (e.g., LEDs with emissions >700 nm) to decrease pupillary constriction of the eye to allow a wider opening for imaging through the pupil or avoid the use of pharmacological dilators altogether.

Figure 10:
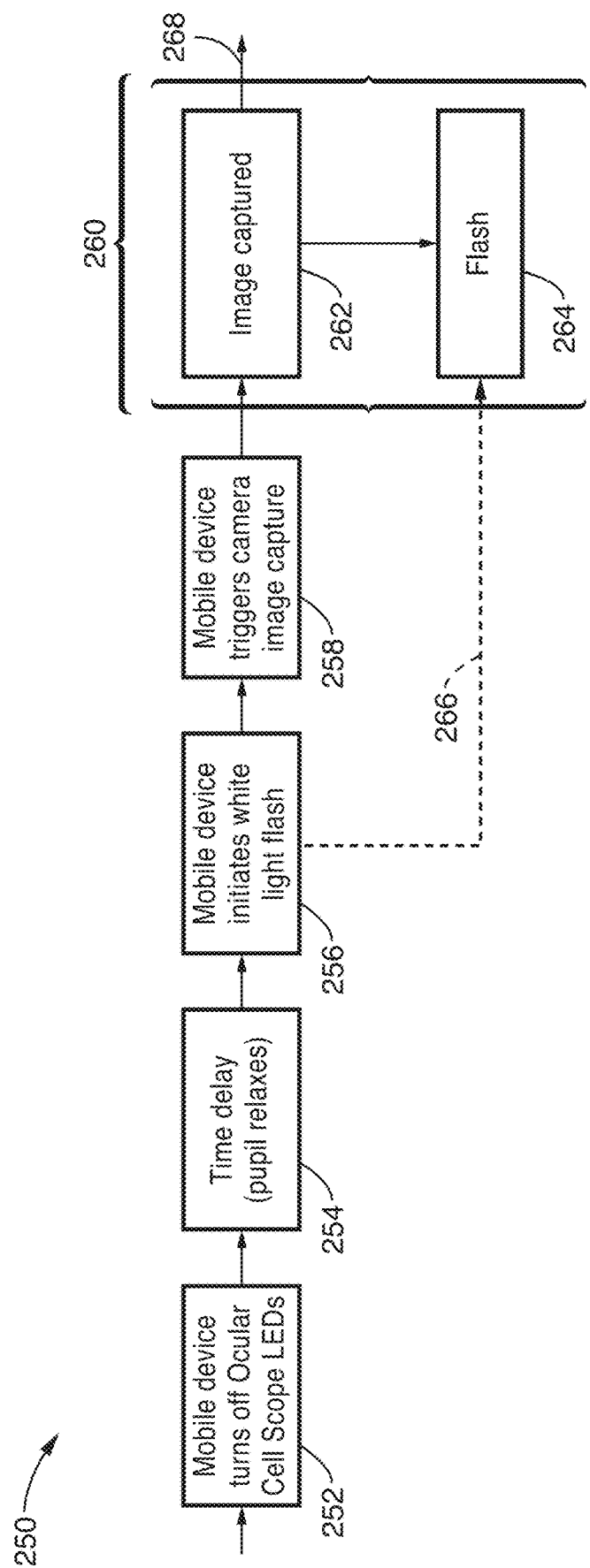
FIG. 10 is a flow diagram of a retinal image capture control in a retinal imaging system according to an embodiment of the present disclosure.

FIG. 10 illustrates an example embodiment 250 of retinal image capture for the presently disclosed ocular imaging device. During this process, the mobile device turns off 252 elements (e.g., LEDs) of the light source ocular cellscope, followed by a time delay 254 to allow the pupil to relax, upon which application programming initiates 256 a light flash (e.g., white light), and triggers 258 camera operation to capture an image to be used in the mosaic. At a selected time delay 266 from the previous flash, an image capture sequence 260 is performed comprising generating a flash 264 in synchrony with image capture 262, with the image capture being output 268 for checking and assembly into a mosaic.

The acquisition software programming for the present disclosure also controls imaging on the mobile device, including focus, color balance and exposure. As described above, light in the infra-red (IR) region can be used to focus and center the image, because human eyes are not capable of sensing IR light, while the camera sensor has that capability. A white light can then be flashed to capture a final color image once the image is focused and oriented using IR light.

However, the unmodified camera sensors of many commercial mobile devices do not permit control over the color balance, white balance, and exposure. In addition to this, most camera modules on commercially available mobile devices now have infrared filters to decrease noise from IR region. To overcome this limitation on some mobile devices, the apparatus may use a monochromatic display element (e.g., LED) to illuminate the retina for fundus imaging. The display element wavelength would preferably have specifications with a peak light intensity in the far red region (650 nm to 750 nm). In this region of wavelengths, the camera is still sensitive to the light emitted and reflected off of the retina. However, the human subject is less sensitive to these wavelengths thereby minimizing photosensitivity and eye movement, as well as minimizing or preventing constriction of the pupil. In particular, this wavelength region of light is outside of, or at the extreme end, of the human visible spectrum.

Furthermore, the intensity of the monochromic display element can be increased to match the exposure requirement needed by the white display element, so that exposure requirement of the monochromic display element will be equivalent to the exposure requirement of the subsequently flashing white display element. This technique will allow the mobile device to both focus and properly expose without irritating the subject being photographed. Color balance can also be achieved using a sensor with unknown and/or variable color balance and demosaicing characteristics with the use of sequential monochromatic illumination.

In one embodiment, the illumination system has a white display element configured to capture a final color image and a far red display element that is configured to be used to set the focus of the system, to provide "preview" illumination and to determine the intensity to be increased to set the exposure to the same level as the white display element. Preferably, the far red display element is chosen to have a peak or a relative intensity that is >0.75 of peak at the peak of (1-photopic response) multiplied by response of camera with filters intact (IR filter, etc.).

In other words, the imaging system in this configuration uses display elements with peak wavelengths (or wavelength that is >0.75 of relative peak wavelength intensity) at a region that is the peak of the following equation: (camera spectral response)×(reflectance of specific region of retina), thereby enabling the maximum response from specific regions of the retina. The specific regions of the retina can include the retinal vasculature (vein or artery), the optic disc, the macula, or the retinal nerve layers.

In a further embodiment, the system optionally includes an image intensifier in the imaging path. The image intensifier can be an image intensifying tube, micro-channel plates, or a thin film or similar component that is placed in the optical train of the system to convert longer wavelength light to shorter wavelength light. Accordingly, the system with the image intensifier is configured to convert IR images into images in the visible wavelength to enable a camera phone that has an IR filter to image the retina.

In various embodiments, single or multiple display elements are controlled, related to, or based on mobile phone or device camera feedback through wireless (Bluetooth or Wi-Fi) or electrical connections. The feedback from the mobile device can be performed closed-loop using software to modify: (a) the intensity of each display element independently; or (b) the combination of display elements turned on or off; or (c) the color balance of the image; and/or (d) the utilization of the dynamic range of the sensor. For example, the imaging system can use a real-time, closed-loop feedback where the software changes the intensity of the illuminating display element(s) to color balance the image before the device user sees the image in the display. Feedback can be provided by an analysis of a software computed image quality metric on acquired images to decide when to move the fixation screen, what images should be retained, how illumination parameters should be changed. Computational analysis of images provides information about what images should be retaken and presents this information to the operator. This reduces many common errors from users that cause images to be blurry, poorly positioned, defocused, or have glare.

In another embodiment, the ocular imaging system can be used in conjunction with fluorescent dyes that have been introduced to the eye or the surrounding structures. The apparatus can control the wavelength, sequence and duration of display element emissions to excite one or more fluorescent dyes. The display element wavelengths will be determined by the dyes that are selected. The preferred display element wavelength emissions for use with fluorescent dyes are in the blue region (450 nm to 500 nm); the violet wavelength region (400 nm to 450 nm); and the ultraviolet (UV) wavelength region (200 nm to 400 nm).

Similarly, the imaging system can use a light source that includes a blue display element (400 nm to 500 nm peak emission) to provide an image based on the autofluorescence of the retina.

Accordingly, the apparatus can utilize display elements with different colors for fluorescence and brightfield imaging and a switch configured to switch between fluorescence and brightfield imaging modes.

The software programming of the apparatus can also have a processing module that generally processes the initial images acquired by the mobile device. For example, some embodiments of the imaging system can capture images of different fields of the retina and then process the images to compile the images to show the entire field of the retina as one image.

Figure 11A:
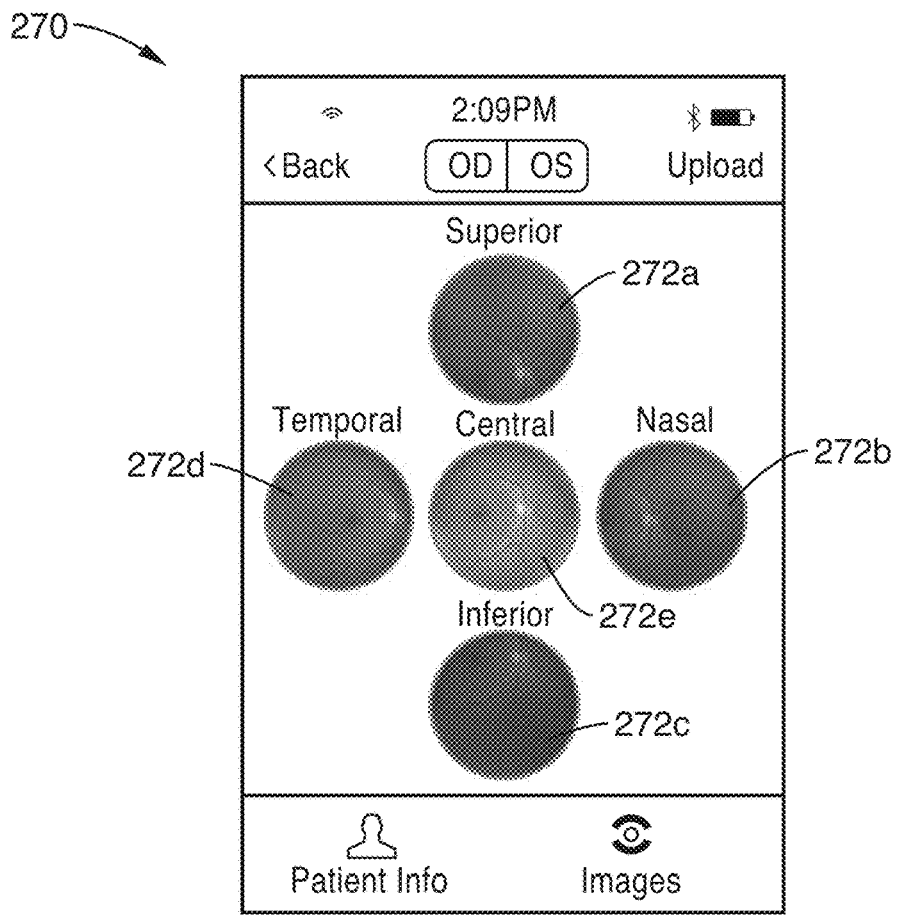
FIG. 11A to FIG. 11B are images of an image stitching process according to an embodiment of the present disclosure.
Figure 11B:
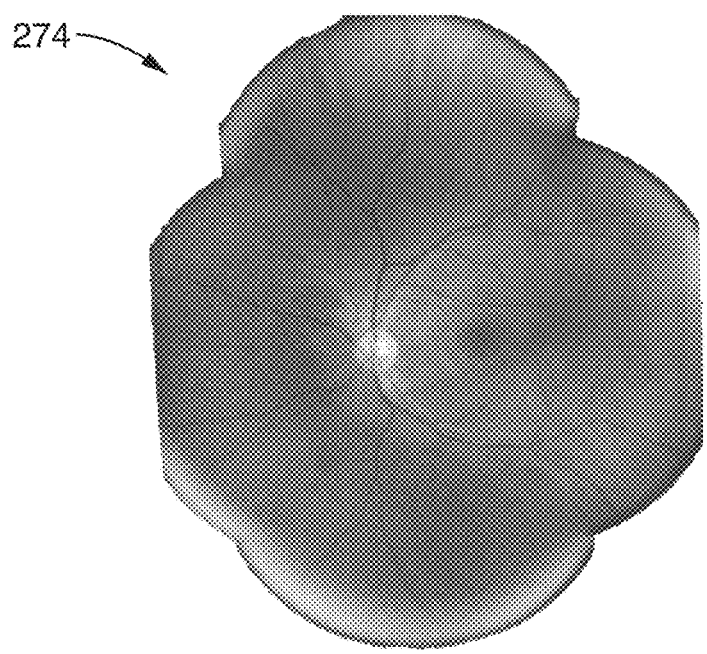

FIG. 11A through FIG. 11B illustrates an example embodiment of an image stitching process. FIG. 11A depicts the start of image stitching 270 with a set of images 272a through 272e which were each captured with a first field of view (e.g., 55 degrees), and are stitched together into the image 274 seen in FIG. 11B which provides a second field of view (e.g., 80 degrees) which is larger than the first field of view.

Figure 12A:
FIG. 12A through FIG. 12G are images captured and processed for referral-warranted diabetic retinopathy according to an embodiment of the present disclosure.
Figure 12B:
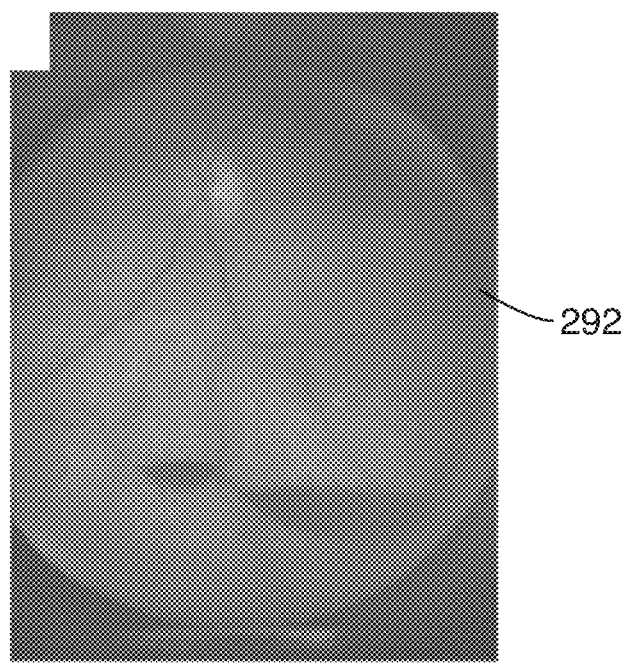
Figure 12C:
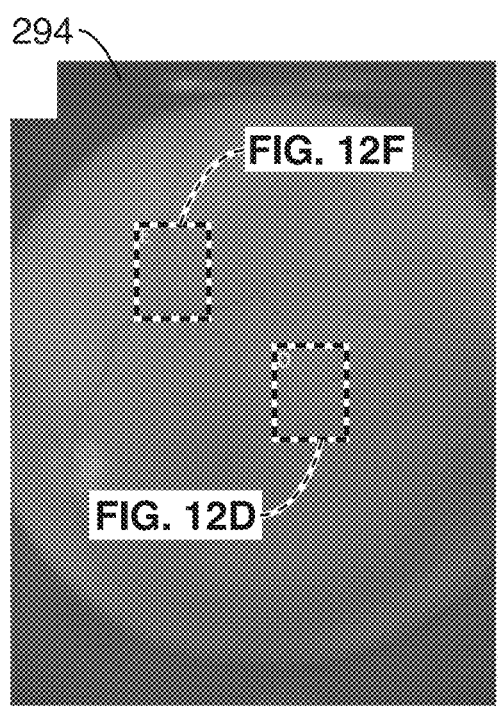
Figures 12D, 12E:
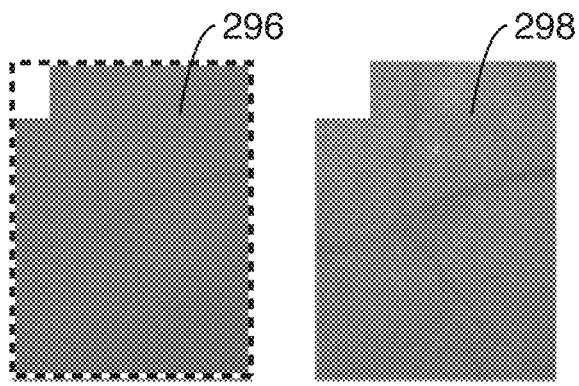
Figures 12F, 12G:
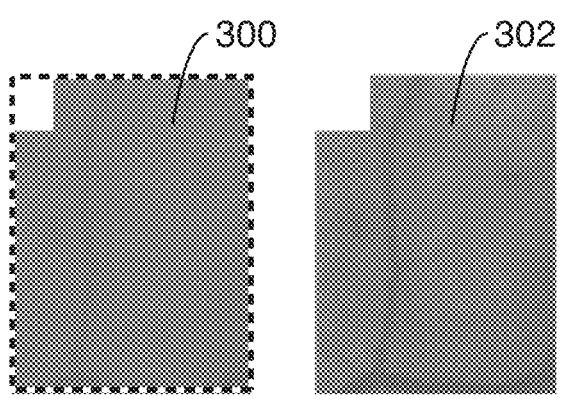

FIG. 12A through FIG. 12G illustrate imaging captured for referral-warranted diabetic retinopathy taken with the disclosed cellscope. Fundus photographs of a diabetic patient's right eye FIG. 12A 290 and left eye FIG. 12B 292 demonstrating old retinal photocoagulation therapy and re-activation of quiescent diabetic retinopathy with pre-retinal hemorrhage. In FIG. 12C 294 a fundus photograph is seen of the left eye in a diabetic patient without known history of diabetic retinopathy. The disclosed ocular cellscope resolves trace signs of neovascularization in FIG. 12D 296 and microaneurysms in FIG. 12F 300. A red-subtraction filter is utilized in the present disclosure to enhance contrast of neovascularization as seen in FIG. 12E 298 and the microaneurysms as seen in FIG. 12G 302.

FIG. 13A through FIG. 13G illustrates an example of the operations of the custom mobile device (e.g., smart phone) application programming and screen shots.

Figure 13A:
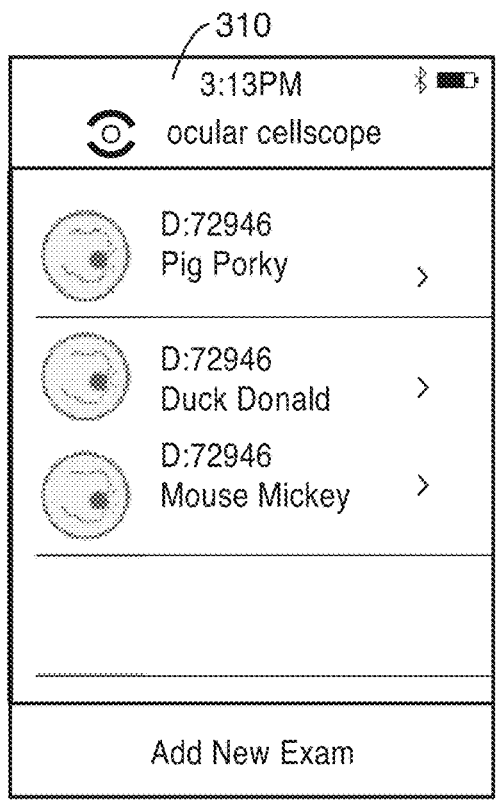
FIG. 13A through FIG. 13G are illustrations of operation of the retinal imaging system according to an embodiment of the present disclosure.
Figure 13B:
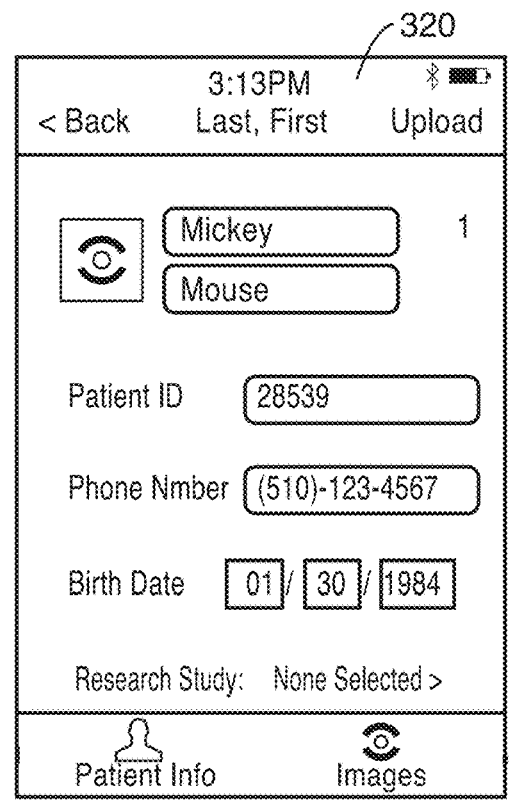

At least one embodiment of application programming for the ocular imaging device of the present disclosure is configured for execution from a mobile device, such as a smart phone. An example application 310 seen in FIG. 13A is configured for selecting a corresponding subject (patient) and their information and demographics in FIG. 13B 320 which would be linked to the captured images. For example, to begin an examination, the operator may tap the 'Add new Exam' button from FIG. 13A, then in FIG. 13B, the user can enter basic patient information.

Figure 13C:
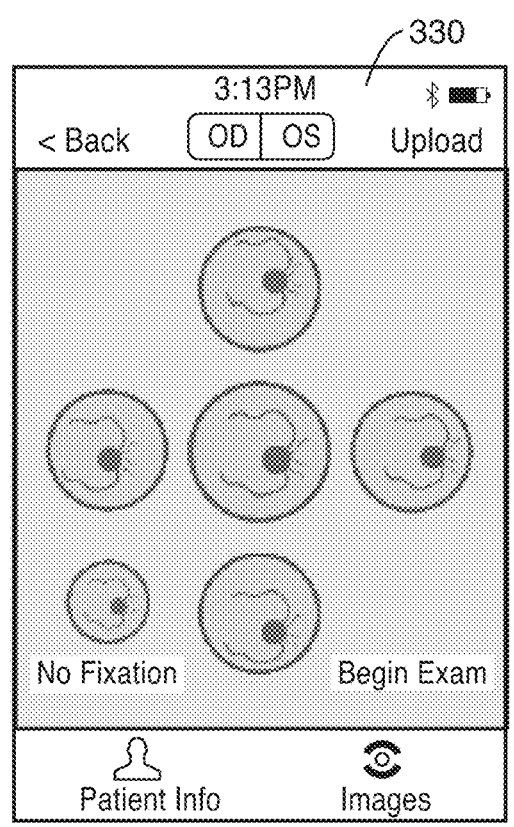
Figure 13D:
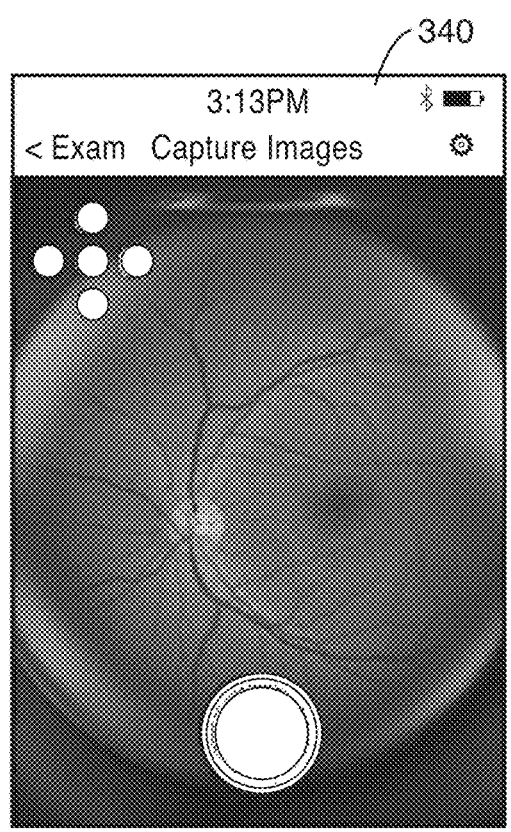
Figure 13E:
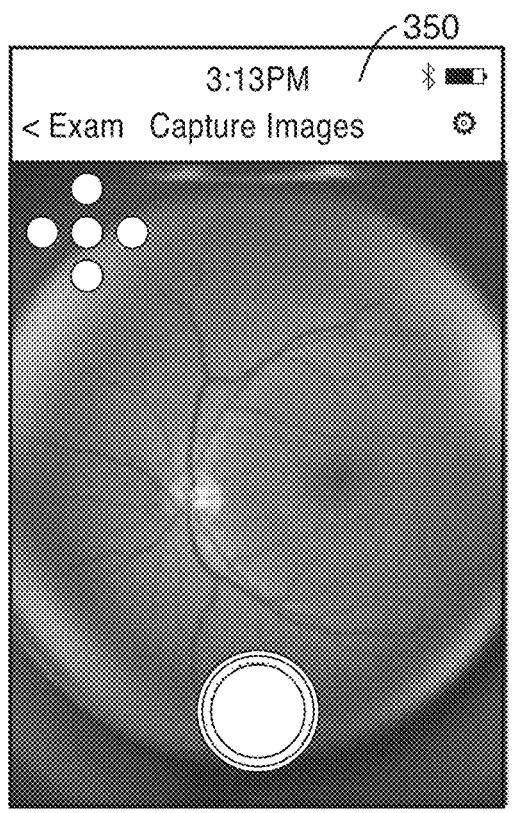
Figure 13F:
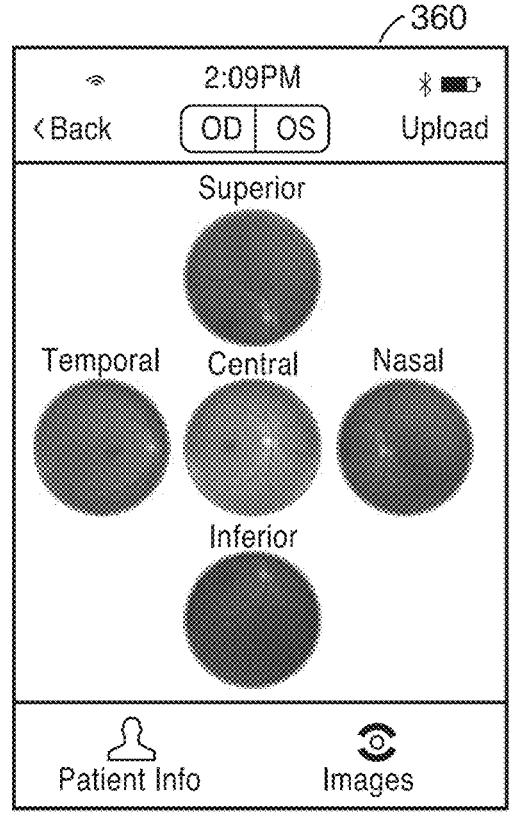
Figure 13G:
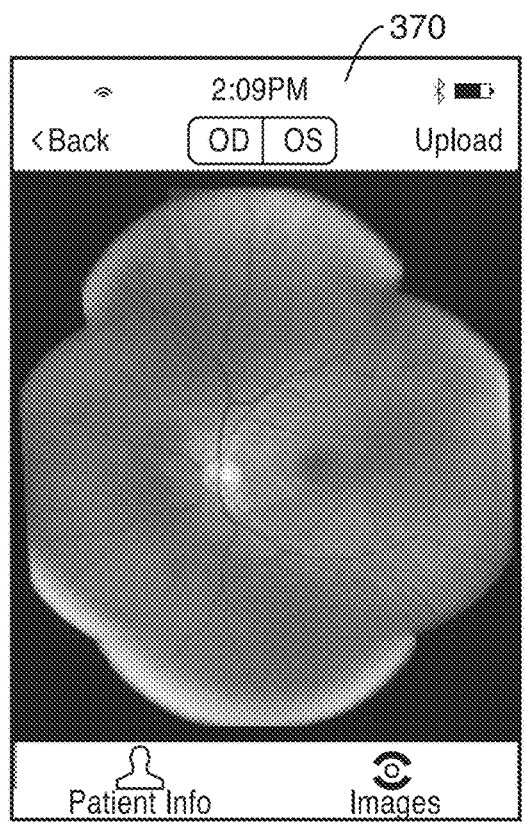

The application programming is configured, as seen in FIG. 13C for controlling 330 the fixation screen based on the area of the retina to be imaged. For example on screen 330 in FIG. 13C, the user can tap the toggle at the top of the screen to select the eye being imaging. On this screen, the user can then tap the desired location of the retina to be imaged (Central, Superior, Nasal, Inferior, Temporal). When the user selects the desired region of the retina to image, the control processor signals the corresponding fixation target on the fixation screen to appear and directs the subject to fixate gaze using the eye not being examined. The application is also configured to preview and then capture and store digital images. A preview mode is entered 340 in FIG. 13D under a first light condition (e.g., low intensity far-red illumination) for surveying and focusing on the retina, a setting that remains comfortable for the subject under sustained periods of illumination. Once camera positioning and focus are optimized, then the system initiates image capture 350 under a second light condition (e.g., high-intensity white flash) as seen in FIG. 13E, and stores the images, such as for example onto the mobile device. Finally, the application programming is configured to stitch 360 the individual photos as seen in FIG. 13F together in creating a composite photo of the retina as seen in FIG. 13G 370. It should be appreciated that in different embodiments, the individual images can be stitched together (a) using the mobile device processor, (b) through cloud-based processing power, (c) other processors, (d) or combinations of processors thereof, to create a wide field composite image.

In another embodiment, the image processing software of the apparatus can use anatomical features (optic disc, pupil, iris, etc.) as a scale for measurement within the images. For example, the scale for measurement as a frame of reference in the captured images can be a scale that is placed in an intermediate plane in the system or a digital scale that is provided by the software.

In at least one embodiment, the processing software also provides multi-spectral imaging in which the captured IR, far red, and color images are overlaid and compared in response to utilizing known image processing operations to identify any features that are visible in one illumination wavelengths that may not be detected in the other illumination wavelengths.

The acquired and processed images may be stored in the device or on removable media, and/or transmitted to a remote location for further evaluation through wired or wireless transmissions (e.g., Wi-Fi, Bluetooth, or cellular network capabilities of the mobile device or through an Ethernet cable).

The communications module of the programming software of the mobile device can prepare and transmit to any number of remote locations for storage or real time evaluation by a third party for remote ocular evaluation (telemedicine) or for medical screening. For example, the captured and processed images can be transmitted and inserted into designated patient electronic medical records. The images can also be transmitted simultaneously to one or more physicians in different locations for a real time evaluation and diagnosis. The ocular imaging system can be used for the remote diagnosis of diseases including diabetic retinopathy, hypertensive retinopathy, glaucoma, age-related macular degeneration, macular dystrophy, retinal detachment, papilledema, macular edema, retinal detachment, retinopathy of prematurity, retinal vascular occlusions, and infectious or parasitic retinal diseases.

As described in a previous section, the fixation screen is used to direct subject gaze, such as toward light emitting, light transmitting, or light reflective screen with high-contrast and capable of software programmatic control. The screen is designed to face the patient and be observed by the eye not under test. As a patient moves their gaze to center a foreground element in their field of view, the eye under test will also move, as was described in relation to FIG. 3A through FIG. 3D. This allows the camera to photograph a different region of the retina. The transformation between the focal-element on the fixation screen and the movement of the retina is estimated but also is empirically calculated based on measurements from the control processor. The inverse of this relationship maps locations of the patient's retina to a unique location on the fixation screen. This relationship forms a feedback loop where the control processor is able to control the positioning of the retina with the fixation screen as an intermediary. This relationship can be used to understand illumination patterns to minimize reflections from the cornea via a lookup table.

Motivations for imaging specific regions of the retina include assembling a wide field image of the retina for detection of various diseases involving the retinal periphery, localizing and monitoring landmarks and pathology including but not limited to nevi, neovascularization, and retinal drusen or hemorrhage known from previous examinations or the current examination. Additionally, software-mediated alignment and stitching of multiple 'small' views of the retina assists in producing wide-field images of the retina without the use of pharmacological dilators (i.e., non-mydriatic imaging). Wide-field mosaics can be continuously expanded or regions re-imaged as needed, as was described in FIG. 9.

Additionally, the focal point brings different regions of the retina into the camera field of view. It should be appreciated that embodiments of the present disclosure are configured for outputting an animated character or any desired foreground element with a background, such as for attracting the gaze of pediatric patients, instead of the use of a simple point or target. This system is beneficial because it allows the control processor to dictate patient gaze and can prioritize or select regions of the retina based on past examinations, findings from the current exam, low quality images or images with artifacts that require photographing a region again for better image stitching. The fixation point may be explicitly determined or requested by the operator, and in at least one embodiment mapped out and stored. The control processor may take immediate or delayed instruction from the operator. Like other control aspects of the device, operator commands given to control processor can be given by voice, audible cue, screen tap, screen multi-touch gesture like swipe, pinch, and spread, or coarse motions interpreted by the operator facing camera. These gestures may be tied to a specific location on the screen, an example is when the user interface presents a button. In this example a tap in the region of the button signals an input. These gestures need not be tied to a specific location to facilitate the operator in swiftly inputting commands to the device without requiring precision or accidental taps. These gestures which don't require specific regions of the screen can reduce unwanted motion Data that describes what the desired gaze was when a picture was taken can be recorded and used to assist with image stitching. For example, as one of many potential ways this information can be used, knowing that two pictures were taken after the focal point moved right to left informs the stitching algorithm which boundary is shared between the two consecutive images to accelerate stitching. Stitching can be improved by including sensor data along with photograph acquisition. Motion changes and inertial motion unit (gyroscope) readings inform the control processor how the device was moved, which provides orientation changes also describing how sequential images are related and accelerating image stitching and reducing power consumption.

An image quality metric is computed on acquired images, including acquired images that are not displayed, recorded, or ever presented to an operator or patient; for example in the process of focusing, or determining orientation. The image quality metric is used to identify which images are suitable for use and which regions of the retina have been sufficiently recorded at that point. Programming for executing the image quality metric is configured to examine regional or global data from the retina. For example, sometimes there may be glare in a region of the photograph but much of the image contains highly detailed recorded image of the retina. These regions can be cropped out, removed in the course of image stitching, or left in without affecting the assessed image quality of the image. The image quality metric can be a critical part of the feedback loop allowing the system and operator know when and how to proceed. The fixation point is usually moved when an image quality score indicates success. This process is useful in reducing the propagation of poor images into stitching or clinical reading for diseases and minimizes unavoidable motion artifacts, glare, defocus, and positioning errors from affecting the examination.

The processor controlled fixation screen is used to not just provide feedback to optimize an individual image but can also optimize the quality of a series of images. Uneven illumination, glare, or motion and distortion at times is not problematic for a single image, but when multiple images are combined and stitched, these artifacts can reduce image stitch quality or present hard to interpret results. Once problematic area/areas are identified by image processing algorithms, the fixation screen can guide the retina into an orientation to acquire images capable of resulting in a higher fidelity stitch. The control processor and software is configured for determining when a picture is inappropriate for image quality reasons and image stitching reasons. In both of these situations, the programming knows where in the retina the photo was originally taken through metadata that lists the location. If an individual photo is not suitable, the programming can present the same fixation point again. If it is the case that two images do not sufficiently overlap, the programming is configured to present a fixation point in the space between the two fixation points of these already acquired images. Artifacts occur, for example, by reason of glare, blinking, motion from any of the users or operators, unique patient physiology or anatomy, and the like.

The imaging system can process information from sensors providing inertial motion, acceleration, as well as real-time image quality (including blurriness, motion, contrast, and brightness) to determine opportune moments to turn ON the illumination system for acquiring an image. Since ambient light levels are low, the illumination system determines image acquisition sharpness as a cofactor analogous to shutter speed. Additionally, this information may be utilized to assist in determining relative position and orientation of images to assist in image stitching. The control processor will ignore photos taken when inertial or positional sensors (such as accelerometer, inertial motion units, gyroscopes, etc.) indicate excessive device motion. The control processor weighs readings from these sensors to decide moments suitable for image acquisition.

Additionally, computational processing and recognition of retinal anatomic structure, including but not limited to the retinal blood vessels, optic disc, fovea can be utilized as fiduciaries for localization and orientation within the retina. In one embodiment, imaging system programming recognizes retinal structures and employs automated repositioning of the fixation target to steer the orientation of the retina. In another embodiment, image system programming recognizes retinal structures to provide overlay or annotation from prior imaging results, thereby assisting in the localization of regions of interest. In another embodiment, imaging device programming utilizes information from any of a gyroscope, accelerometers, compass, and or similar motion/position sensing devices to provide image orientation information during image acquisition and to assist in software-mediated alignment of image composites. This process may also be performed in real-time, wherein image unit programming continually guides the fixation target and constructs a growing composite and wide-field image of the retina.

The screen of the mobile device (smartphone) coupled to the presently disclosed ocular device is utilized to mirror real-time images from the camera allowing the operator to align the camera with the patient's (subject's) eye. Common smartphone interfaces present opportunities for the operator to potentially override automated modes to offer fine-control of image acquisition parameters like exposure, focus, retinal regions of interest, which are registered and recorded to associated patient information. Additionally, the screen can receive a variety of touchscreen commands.

Imaging device programming may utilize the focus control of current mobile devices to capture images in a rapid, automated fashion wherein multiple images are serially acquired at different focal planes. In one embodiment, this process may be used to capture multiple images near the retinal plane, improving the probability that at least a subset of images will be in focus. This approach is of particular use with handheld imaging systems, as small motions of the examiner (user) or patient (subject) can easily result in loss of focus and decreased image quality.

In another embodiment, serial images are acquired while the depth of focus is intentionally drawn away from the retina to provide three-dimensional information about intraocular structure. This three-dimensional information then may be reviewed in several fashions. In one embodiment, the image data is reviewed dynamically as a video which may help to identify retinal tears or detachments that lift away from the focal plane of the normal retina, excavation of the optic nerve, and presence of vitreal debris. In another embodiment, imaging processing techniques are used in the system to remove blurred regions of an image, and to selectively montage the in-focus regions of images acquired in series across a focal range.

Additionally, selective illumination including, but not limited to slit beam or spot illumination, may be combined with the above-mentioned imaging programs to help optically isolate three-dimensional structures of interest during image acquisition. In another embodiment, fixation-guided imaging may be employed to capture serial images with small, in-focus displacements of the retina. Two images may be viewed simultaneously with readily available binocular viewers, including but not limited to virtual reality goggles or three-dimensional displays, to allow visualization of three-dimensional structure in the retina. In another embodiment, two such images with small spatial displacement are presented on a viewer with high frequency cycling (>1 Hz) to enable depth-of-field perspective through a technique known as 'wiggle stereoscopy.'

Figure 14:
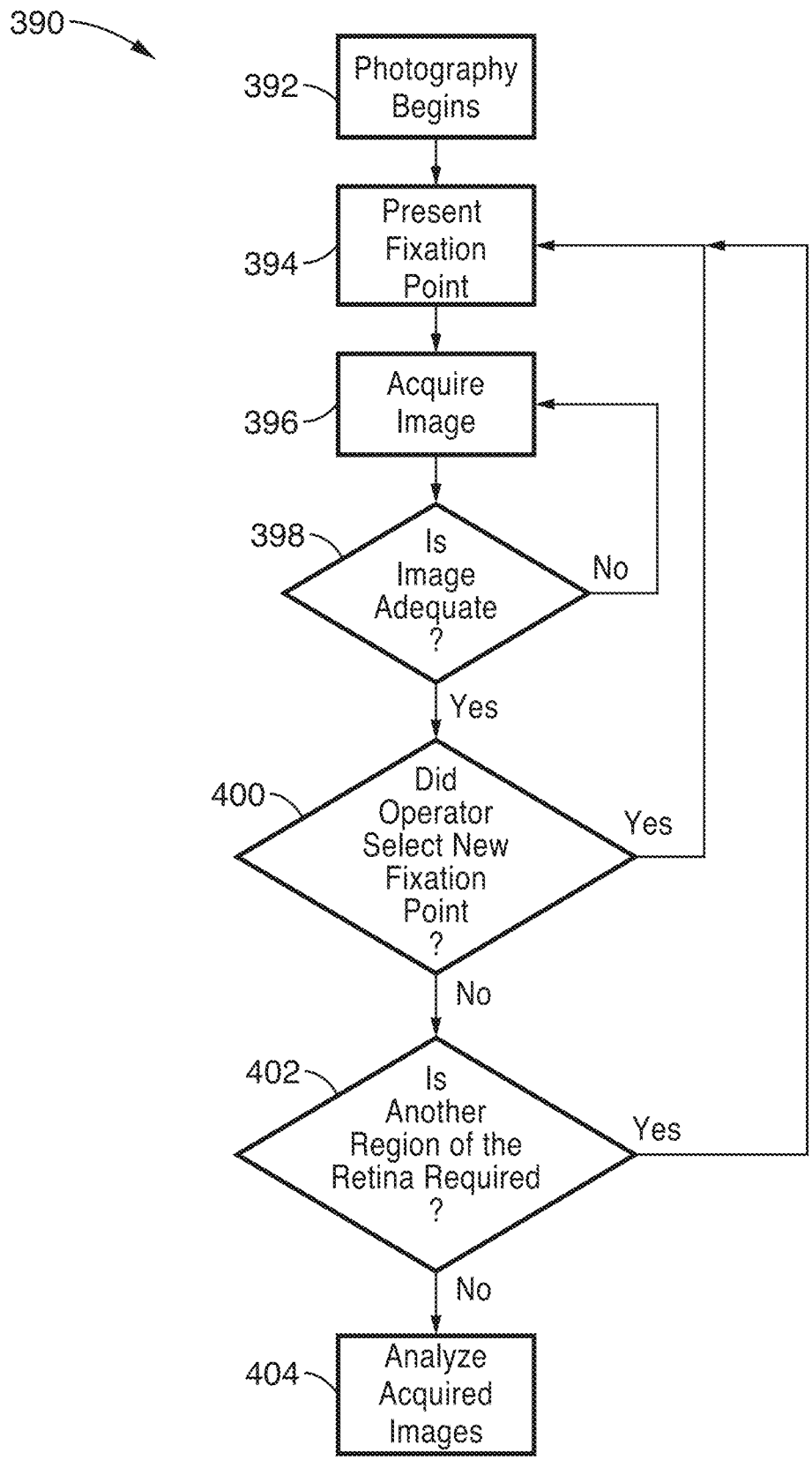
FIG. 14 is a flow diagram of device operation of the retinal imaging system according to an embodiment of the present disclosure.

FIG. 14 illustrates an example embodiment 390 showing retinal photography steps for the present disclosure. When the device is in the operating mode for capturing images, the programming of the system is preferably configured for making a number of decisions to assist the operator in obtaining high quality images. It initiates a first illumination scheme, if multiple illumination schemes exist. This illumination scheme can have an associated image quality metric. One example of a first illumination scheme is in focusing, where a wavelength of light is chosen to minimize pupillary constriction and the device captures a number of images to ensure the device is in focus. System programming can await for opportune moments until the software determines the device is reasonably still (e.g., stable and stationary) by interpreting readings from the accelerometer, gyroscope, and/or similar motion/positioning/pose sensing device. If the device is operating in such a mode where multiple illumination schemes are required, it will enter the next in a series of potentially multiple illumination schemes.

These steps are seen outlined in the figure as photography (image capture) 392 begins, a fixation point is presented 394 to the subject, and an image is acquired 396 (optional preview mode is not shown for sake of simplicity of illustration). A check 398 is made if the image is adequate, and if it is not, then a return is made to step 396. Otherwise, with an adequate image a check 400 is made to determine if a new fixation point has been selected (indicating more images are desired). If a new fixation point is selected, then execution moves to step 394 to present that fixation point and proceed through the image capture steps. Otherwise, if a new fixation point was not selected at block 400, then a check 402 is made to determine if imaging of another region of the retina is desired (required). If there are more regions to image, then execution returns to step 394 to perform additional imaging, otherwise image capture is completed and acquired images are analyzed 404.

Figure 15:
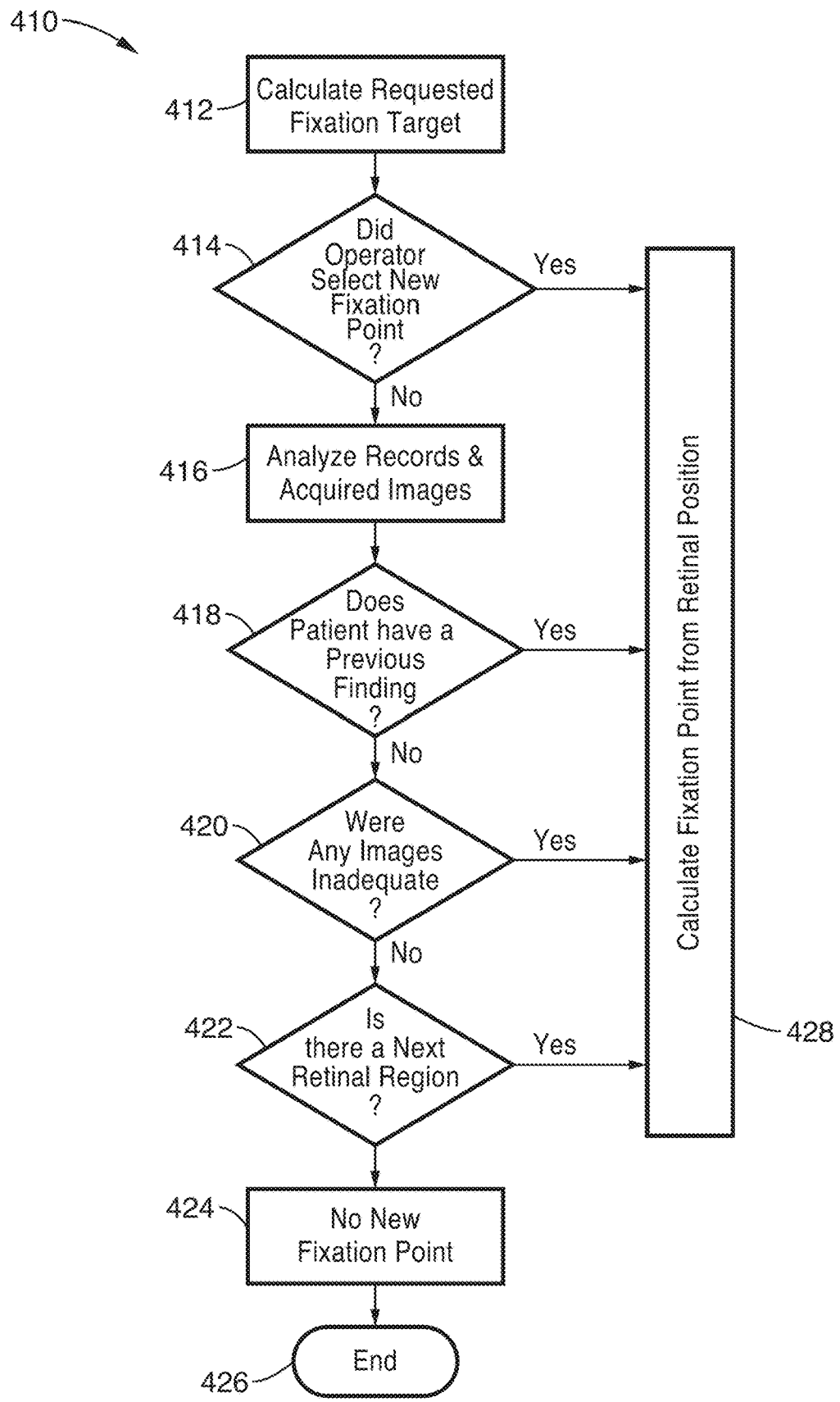
FIG. 15 is a flow diagram of device operation of the fixation screen of the retinal imaging system according to an embodiment of the present disclosure.

FIG. 15 illustrates an example embodiment 410 of operation of the fixation screen which provides feedback for scanning the retina of the subject. The fixation screen provides a method for scanning the patient's retina. The control software is configured for requesting a change in patient's gaze for a number of reasons, which include but are not limited to (a) obtaining images from adjacent areas to improve image stitching, (b) imaging neighboring areas of the retina, (c) imaging of specific areas (e.g., based on history and/or detected conditions), (d) image regions of missing or poor image quality in a widefield montage, (e) to image a region of interest with several orientations, (f) to assemble a video of adjacent images scanning the retina, or similar. A widefield scan of the retina entails ensuring that a plurality of regions of the retina are imaged and then stitched together.

The example embodiment depicts determining a requested fixation target 412, followed by a decision to determine 414 if the operator selected a new fixation point. If a new fixation point was selected, then execution moves to block 428 to calculate the fixation point required to image the desired retinal area. If no new fixation points was selected by the operator, then execution moves from block 414 to block 416, in which records and acquired images are analyzed, and a determination 418 is made to determine if the patient had a previous finding. If there was a previous finding, then execution moves to block 428 to calculate the fixation point required to image that area. Otherwise, if no previous findings, then execution moves to block 420 where a check is made to determine if any of the images were inadequate. If a problem was found with any images, then execution moves to block 428 to determine the proper fixation point for that image. Otherwise, if images are adequate, then execution moves to block 422 where a check is made to determine if there are additional retinal area regions to image. If additional retinal areas need imaging, then execution moves to block 428 to determine a proper fixation point for the next area. Otherwise, if none of these needs for a new fixation point are met, then execution has reached block 424 with no new fixation points and this process ends 426.

Figure 16:
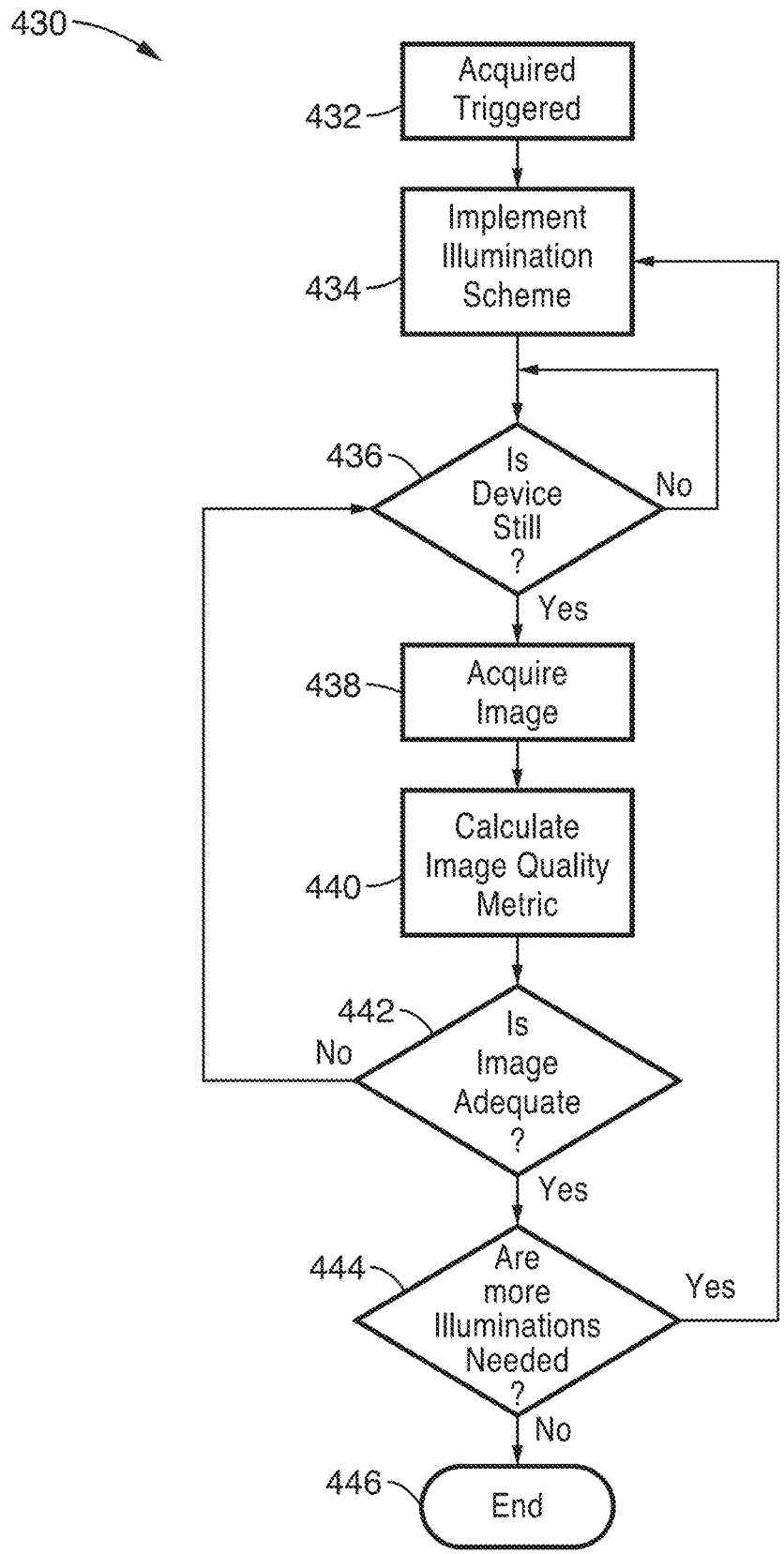
FIG. 16 is a flow diagram of device operation of system control during image acquisition according to an embodiment of the present disclosure.

FIG. 16 illustrates an example embodiment 430 of system control during image acquisition, showing capturing of a single retinal image, indicating a feedback path by which the image is evaluated for quality (e.g. glare artifacts, as indicated by an image quality metric calculation) and subsequent re-imaging with varying illumination schemes (e.g. illumination and/or collection path annuli of various sizes, or different wavelengths, intensities, or the like) is performed until adequate image quality is obtained for the region imaged. Image acquisition is triggered 432, and the illumination scheme is triggered 434, followed by a determination 436 if the device is still (stationary) toward capturing a valid image. If the device is not still then a delay occurs looping back to step 436 until the device is found to be still. With a still device, an image is captured 438 upon which an image quality metric is determined 440 and a check is made if the image is adequate 442. If the image is not adequate, then a jump if made to step 436 to obtain another image when the device is still. Otherwise, a check is made 444 to determine if more illumination/image capture sequences are needed. If there is another image to capture, then processing moves back to block 434, otherwise this processing ends 446.

4. Example Embodiments 4.1 Example 1

The technology described herein may be better understood with reference to the accompanying examples, which are intended for purposes of illustration only and should not be construed as in any sense limiting the scope of the technology described herein as defined in the claims appended hereto.

In order to demonstrate the operational principles of the apparatus and system, a retinal camera apparatus based on a mobile phone was constructed. The camera included a custom-designed mobile phone attachment (ocular imaging device) that housed optics capable of capturing a retinal field-of-view of approximately 55 degrees. The device provided wide field imaging, enabling convenient and high-resolution diagnostic imaging for a broad set of applications.

The housing contained the illumination and collections optics, and an integrated phone holder that ensured alignment of the optics with the camera on the phone. The acrylonitrile butadiene styrene (ABS) plastic housing was designed and constructed for use with an iPhone 4S®, iPhone 5S®, or iPhone SE® mobile phone. The phone required no modification, and the mobile phone could easily slide in and out of the holder. A rubber cup on the lens eyepiece rested on the orbital rim of the sitting or supine subject, providing user-controlled stabilization of the apparatus.

Retinas of human test subjects were imaged through a 54-diopter ophthalmic lens. The ophthalmic lens of the apparatus formed an intermediate image that was relayed by a 20 mm focal length achromatic lens to the camera of the mobile phone. The housing contained optics for illuminating and imaging the retina onto the camera of a smartphone. A polarizing wire grid beam splitter was used to illuminate the retina with polarized light and minimize unwanted reflections.

An aspheric condenser lens transmitted light from the LEDs to a diffuser. The light passes through a polarizer oriented parallel to the vertical axis of the beam splitter, an annular mask with 8 mm inner diameter and 15 mm outer diameter, and a 50 mm focal length condenser lens. The illumination light was reflected by the beam splitter and passes through a 54-diopter ophthalmic lens to form an annulus with a 4.8 mm inner diameter and 9.6 mm outer diameter at the surface of the cornea. The illumination light defocuses and uniformly illuminates the retina, on which it is scattered and depolarized. Light from the eye is collected and transmitted through a second polarizer thereby preferentially blocking polarized illumination light and reflections. An achromatic lens with a focal length of 20 mm relayed signal to the smartphone camera module.

The prototype device was powered by a rechargeable lithium polymer battery and included a compact, custom-printed circuit board containing a microcontroller module, Bluetooth transceiver, two buck/boost controlled-current LED drivers, battery management controller, power supply, and several status indicator LEDs. The battery, electronics, and illumination optics were miniaturized and arranged in linear fashion along the optical axis to fit within the handle of the device. An external OLED display provided a fixation target for the contralateral eye. This external display attached to either side of the device housing using magnets. Spring-loaded gold pins provide electrical contact for power and communication to the microcontroller. To conserve in-the-field battery life, the system automatically shut off after a period (e.g., five minutes) of inactivity.

A custom iPhone app was developed which communicates with the electronic hardware via Bluetooth low-energy (BLE). This application flowsheet was shown in FIG. 13A through FIG. 13G. When the user selects the desired region of the retina to image, the control processor signals the corresponding fixation target on the fixation screen to appear and direct the subject gaze using the eye not being examined. The application provides a preview window where the operator employs ergonomic touch and swipe motions to adjust focus, zoom, and exposure prior to initiating the image capture sequence. This approach assists in rapid image acquisition and reduces operator motion that can degrade image quality when using a handheld platform. Additionally, the device uses a low-intensity, far-red illumination setting for surveying and focusing on the retina, a setting that remains comfortable for the subject under sustained periods of illumination. Once camera positioning and focus are optimized, image capture is initiated with a high-intensity white LED to flash during acquisition. Once an exam is completed, the application can store the retinal images corresponding to the specific retinal regions. If desired, images can be directly uploaded from the app to a secure server using Wi-Fi or cellular service for remote reviewing.

The hardware-software integration enables wide-field imaging of the retina in an easy and semi-automated fashion. The device is designed to allow the operator to comfortably hold and operate the touchscreen app using one hand (FIG. 6). The magnetically mounted screen displays a software-driven target (FIG. 3A through FIG. 3D) for eye fixation to minimize unwanted eye movement during examination. Conjugate eye movements simultaneously reposition the imaged eye for rapid and precise imaging of multiple retinal fields. In one example automated program, five overlapping images are captured of the central, inferior, superior, nasal, and temporal retina in rapid sequence. Each image has an approximately 50-degree field-of-view and may be computationally merged on the smartphone to create an approximately 100-degree, wide-field montage, such as was seen in the retina FIG. 13G.

The image-stitching algorithm uses the OpenCV C++ image-processing library to complete the stepwise process. First, radial pincushion and barrel distortion from the optical system is corrected. Second, an alpha mask is applied to crop the circular retinal field of view from each rectangular image. Third, affine transforms are estimated between neighboring fields using Speeded Up Robust Features (SURF) keypoints matching. These transforms describe the translation, rotation, and skew of each peripheral field relative to the central field. To save on computational resources, the transform is estimated using downsampled grayscale images derived from the green color channel. Finally, a full-resolution mosaic is generated using these estimated transforms. Overlapping regions are preferably linearly blended. Individual images or montages may be reviewed on the phone using touchscreen pinch zoom and pan gestures. All image acquisition and processing steps may be performed on the device without requiring an external computer.

4.2 Example 2

To assess the potential for the device as a telemedicine tool, diagnostic quality images of diabetic retinopathy and active CMV retinitis were captured from dilated patients in Thailand and transmitted directly from the mobile phone devices to a secure server. These images were of sufficient quality to enable the remote ophthalmologist in the United States to accurately provide a real-time diagnosis of the retinal diseases.

The mobile phone-based retinal camera apparatus enabled the capture of fundus images remotely. When used through a dilated pupil, the device captures a field-of-view of approximately 55 degrees in a single fundus image. The images were captured on 2652×2448 pixel camera sensor, resulting in approximately 48 pixels per retinal degree. This surpasses the minimum image resolution requirement of 30 pixels per degree suggested by the United Kingdom National Health Service for diabetic retinopathy screening.

In some cases, images captured by the mobile phone-based retinal camera were also stitched together using i2k Retina software (DualAlign LLC, Clifton Park, N.Y.) to create a composite image that captured a larger field-of-view of the retina. This mosaic compared well with a mosaic created using images taken with a TRC-50EX retinal camera (Topcon Medical Systems, Oakland, N.J.) when contrast and exposure were similarly scaled.

The cross-polarization technique was also used and evaluated. Use of the technique reduced, but did not eliminate the reflection from the back surface of the ophthalmic lens. In addition, the cross-polarization technique utilized by the device was shown to increase the visibility of the choroid, optic disc, and blood vessels and also accentuate nerve fiber layer defects by reducing nerve fiber layer reflectivity. However, the cross-polarization also decreased the specularly reflected light from the internal limiting membrane that can be helpful for photography of certain retinal pathology.

The present disclosure provides a number of features and embodiment which provide for each of the following.

A portable device for imaging the fundus of the eye; said device comprising: (a) an optical system for directing illumination into the posterior of the eye and collecting light from the pupil of the eye and imaging it onto a digital image sensor, wherein the collection light path has a computer-controlled focus adjustment, and wherein portions of the illumination and collection light path overlap; (b) software controls for any or all of: the illumination of the eye, the focus adjustment of the collection-path optics, the digital image acquisition, illuminated and or light-emitting fixation elements to direct patient gaze, and the display of control options to the operator; (c) illumination and image collection parameters (including, but not limited to: focus adjustment; illumination light intensity, pattern, position, timing, and duration) which are controlled by a combination of algorithm and operator input; (d) video imaging of the fundus of the eye can be displayed to the operator for purposes of alignment and adjustment of the system to the patient under test; (e) multiple images may be acquired and stitched together in software to create an effective field of view of the fundus comprising ≥55 degrees full-angle.

The device is capable of upload and download of patient and operation data via a cellular data (including but not limited to M2M, 4G, LTE) or wireless communications network, including WIFI, Bluetooth, or other wireless communication protocols.

A fundus imaging device that is hand-held and harnesses both the imaging and computational control provided by a handheld (mobile) computational device.

A fundus imaging device in which the fixation elements are provided by device controlled illumination transmitted through the pupil of the eye under observation.

A fundus imaging device in which the fixation elements are provided by external illumination visible to the opposite eye (the eye not under observation by the fundus imaging device).

A fundus imaging device in which the imaging unit software further comprises a feedback loop between the imaging unit and the position of the fixation point, such that the location of the fixation point may be manually or automatically adjusted to bring desired regions of the retina into view.

A fundus imaging device in which the feedback between the imaging system and the internal target or external display are used to localize, monitor, and track exact landmarks and pathology including, but not limited to, nevi, neovascularization, and retinal drusen or hemorrhage known from either a previous or the current examination.

A fundus imaging device in which feedback between the imaging system and the internal target or external display are used to direct imaging and/or fixation elements to enable improved and/or re-imaging of areas of the fundus poorly stitched in earlier imaging or for which an artifact (such as image glare or patient blinking) corrupted the initial image data.

A fundus imaging device in which the imaging unit programming further comprises a feedback loop between the imaging unit and the illumination unit to alter image characteristics by modifying the intensity of multiple illumination and/or fixation elements independently or controlling the combination of illumination and/or fixation elements that are turned on or off.

A fundus imaging device in which the imaging unit programming further comprises a feedback loop between the imaging unit and the illumination and/or fixation elements to determine the regions of the retina that are being imaged such that regional images can be compiled to show the entire field of the retina as one image by the imaging unit programming, e.g., by stitching of multiple images centered at different retinal coordinates.

A fundus imaging device of any preceding claim, wherein electrical or wireless communication between the imaging system and an internal target or external display used for fixation allow feedback so that there is correlation between a retinal map in software and the target or display allowing regions of retina that have been inadequately imaged to be further visualized and/or re-imaged by calling on specific regions of the target or display to appropriately direct patient gaze.

A fundus imaging device in which an operator provides control guidance through swipe gestures and taps that are independent of a specific location on the screen interface and are sensed through either screen contact, device accelerometers, or the operator facing camera thereby providing fast image adjustments with no, or minimal, contact to the device that could degrade image quality.

A fundus imaging device in which the operator provides control guidance through verbal commands or auditory cues to control functionality and in cases inform both control software and the patient to change behavior simultaneously including but not limited to changing patient gaze and bringing specific regions of the retina into view.

A portable device for imaging the fundus of the eye; said device comprising: (a) an optical system for directing illumination into the posterior of the eye and collecting light from the pupil of the eye and imaging it onto a digital image sensor, wherein the collection light path has a computer-controlled focus adjustment, and wherein portions of the illumination and collection light path overlap; (b) software controls for all of: the illumination of the eye, the focus adjustment of the collection-path optics, the digital image acquisition, illuminated and emitting fixation elements to direct patient gaze, and the display of control options to the operator; (c) illumination and image collection parameters (including, but not limited to: focus adjustment; illumination light intensity, pattern, position, timing, and duration;) which is controlled by a combination of algorithm and operator input; and (d) multiple images are automatically acquired and stitched together in software to create an effective field of view of the fundus comprising ≥55 degrees full-angle.

A fundus imaging device whose illumination unit further comprises a wireless receiver configured to receive wireless control commands from the imaging unit computer processor programming.

A fundus imaging device in which the imaging device programming correlates known fixation point location to regions of the retina, thereby providing relative image position information to assist in software-mediated alignment and stitching of multiple images of the retina.

A fundus imaging device in which in imaging device programming utilizes information from any of a gyroscope, accelerometers, compass and/or similar motion/pose/positioning sensor to provide image orientation information to assist in software-mediated alignment and stitching of multiple images of the retina.

A fundus imaging device in which imaging unit programming moves the fixation point continuously while capturing video and fuses video frames to provide a larger image of the retina.

A fundus imaging device in which imaging unit programming assists in software-mediated alignment and stitching of multiple images of the retina acquired without requiring pharmacological dilators (i.e., acquired with non-mydriatic imaging).

A fundus imaging device in which the imaging system uses a software computed image quality metric to determine when to acquire an image, when to move the fixation point to repeat an image, or which of several acquired images to retain, thereby minimizing positioning errors, motion artifacts, glare, and/or defocus that degrades imaging quality.

A fundus imaging device in which imaging device programming utilizes information from any of a gyroscope, accelerometer(s), compass and/or similar motion/pose/positioning sensor to assist in determining when to acquire an image, or which of several acquired images to retain, thereby minimizing positioning error, motion artifacts, or defocus that degrades imaging quality.

A fundus imaging device in which imaging device programming utilizes information from an image taken in one illumination condition, including any of illumination wavelength, anatomy of the eye illuminated, or area of the fundus illuminated, to automatically optimize conditions for a subsequent image comprising both the exposure level of the camera sensor and the illumination condition, including any of illumination wavelength, area of the pupil illuminated, or area of the fundus illuminated, through use of lookup tables and/or imaging unit programming.

A fundus imaging device in which the imaging unit programming uses retinal structure as fiduciaries, including but not limited to blood vessels, optic nerve, fovea, as well as data from any or all of an gyroscope, accelerometer(s), compass and/or similar motion/pose/positioning sensor, to provide relative location and orientation information within the eye that may assist in real-time stitching of images acquired of the retina.

A fundus imaging device in which imaging unit programming uses retinal structure as fiduciaries, including but not limited to blood vessels, optic nerve, fovea, as well as data from any or all of an accelerometer, gyroscope, and compass, to overlay annotations (i.e., circles, arrows) from prior images in appropriate locations on current image or video acquisition while surveying the retina in real-time.

A fundus imaging device which further comprises any combination of the following.

Provision is made for two- or three-dimensional (2D or 3D) reconstruction of features in the eye based on the image stack or 3D image information obtained, using for example image stitching, maximum-intensity projection, or other algorithmic image reconstruction.

A fundus imaging system in which the 3D image data is obtained via taking multiple images at different focus planes and algorithmically using the image stack to derive 3D image data, and in which the plane of focus is automatically adjusted by changing the autofocus properties of the fundus imaging device via software control.

A fundus imaging device which in conjunction with video or repeated image acquisition, the imaging system focus is moved toward and away from the retina in a continuous motion or series of steps in order to enhance three-dimensional information including, but not limited to, retinal detachment, cup-to-disc ratio, vitreal debris (e.g. 'floater' or hemorrhage).

A fundus imaging device of any preceding claim, wherein 3D imaging information is obtained via adjusting the angle of illumination through the pupil or angle of collection from the pupil for imaging, using prisms, mirrors, or a mechanically adjustable optical path, in order to capture different perspectives of the retina and highlight three-dimensional structure of, and anterior to the retina.

A fundus imaging device in which a slit or annular illumination enhances imaging of three-dimensional structures of, and anterior to the retina. Three-dimensional structure and depth-of-field may be viewed using a three-dimensional viewer (including but not limited to virtual reality glasses) to visualize two images acquired in rapid succession, one with the right eye and one with the left. Small displacements in serial images enable perspective with depth-of-field;

A fundus imaging device in which three-dimensional structure and depth-of-field are presented to an operator of the device using a three-dimensional viewer or high frequency cycling (>1 Hz and <60 Hz) of two images taken with a small displacement to enable perspective with depth-of-field ("wiggle stereoscopy").

A fundus imaging device having an externally-mounted display (such as an LCD, LED, or OLED display) providing a target point for the subject to fixate on using the contralateral eye, allowing specific regions of the retina to be imaged and where said display is under control of software running on the imaging device.

The fundus imaging device of any preceding claim, wherein an externally-mounted display (such as an LCD, LED, or OLED display) provides a target point for the subject to fixate on is removable and can be swapped from one side of the instrument to the other depending on which eye is to be imaged.

A fundus imaging device in which the display attaches magnetically on either side of the instrument.

A fundus imaging device in which the display electrically connect to electronics within the instrument via spring-loaded pins.

A fundus imaging device in which the display communicates with electronics within the instrument wirelessly.

A fundus imaging device which uses one or more lenses, positioned in front of the display to assist the hyperopic or myopic eye to visualize the fixation point.

A fundus imaging device having one or more light emitting diodes that are positioned off-axis at a position in the optical path that provides a target on which the subject being photographed can fixate using the concurrently imaged eye, allowing specific regions of the retina to be imaged.

A fundus imaging device in which the fixation display is removable and can be moved to different locations on the exterior of the imaging device (e.g., different sides) while being held onto the primary assembly by a catchment (e.g., mechanical or magnetic) and maintain a data connection to the primary control unit (e.g., via wireless RF, audio, or electrical contacts built into the mounting points) or automatically reconnect when attached to each fixation point.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the listing of embodiments including the following:

1. A portable retinal imaging apparatus for fundus imaging of an eye, said apparatus comprising: (a) a light source configured for directing light along an illumination path of said retinal imaging apparatus; (b) an optical system configured for collecting light from a pupil of a subject eye being imaged and directing that light along an imaging path onto a digital image sensor configured for capturing an image; (c) a light splitter forming a junction between said illumination path and said imaging path, wherein illumination from said light source is directed along said illumination path to said light splitter which redirects illumination into said imaging path into a posterior region of the subject eye being imaged; (d) a fixation display configured for displaying a fixation target for directing the eye of the subject which is being imaged; (e) a processor coupled to said light source and said digital image sensor; and (f) a non-transitory memory storing instructions executable by the processor; (g) wherein said instructions, when executed by the processor, perform steps comprising: (g)(i) outputting said fixation target from said fixation display so that light is collected along said imaging path from a first retinal area of the eye; and (g)(ii) triggering a flash of light from said light source in synchrony with capturing a retinal image on said digital image sensor.

2. The apparatus of any preceding embodiment, wherein said instructions configured for executed by the processor after step (g)(ii) in claim 1, further comprises: (a) outputting said fixation target from said fixation display so that light is collected along said imaging path from another retinal area of the eye; (b) triggering a flash of light from said light source in synchrony with capturing an image on said digital image sensor from this other retinal area of the eye; and (c) repeating steps (a)-(b) to capture multiple retinal areas of the eye which can be stitched together into a composite image having a field of view wider than the image captured on said digital image sensor.

3. The apparatus of any preceding embodiment, wherein said light source is further configured with a secondary source of light for use during a preview mode.

4. The apparatus of any preceding embodiment, wherein said instructions configured for executed by the processor, further comprises: (a) entering a preview mode in which said secondary light source is activated; (b) collecting light along said imaging path for receipt by said digital image sensor; (c) displaying still or video images of the eye as received by said digital image sensor; and (d) changing said fixation target to move the eye of the subject until a desired portion of the retina is positioned along said imaging path, prior to triggering a flash of light from said light source in synchrony with capturing a retinal image on said digital image sensor.

5. The apparatus of any preceding embodiment, wherein said secondary source of light is generated at a sufficiently low intensity and/or of a wavelength which is sufficiently separate from a visible spectrum of the eye, to prevent changing the imaging conditions of the eye.

6. The apparatus of any preceding embodiment, wherein said secondary source of light comprises a low intensity light source at a far red portion of the light spectrum to which the eye is sensitive.

7. The apparatus as recited in claim 1, wherein said fixation display is visible to another eye of the subject which is not being imaged on said digital image sensor.

8. The apparatus of any preceding embodiment, wherein said apparatus is configured for either manual or automatic location adjustment of said fixation target to bring desired retina regions of eye into view on said digital image sensor.

9. The apparatus of any preceding embodiment, wherein said apparatus is configured for being mechanically and optically coupled to a mobile electronic device containing a digital image sensor and configured for executing application programming for capturing retinal images on said digital image sensor.

10. The apparatus of any preceding embodiment, wherein said apparatus is configured for being controlled in response to communications from the mobile electronic device.

11. The apparatus of any preceding embodiment, wherein said apparatus is configured for changing the fixation target, and lighting output in response to swipe gestures and taps on the display screen of said mobile electronic device.

12. The apparatus of any preceding embodiment, wherein said instructions configured for execution on the processor, further comprises detecting a motion of the apparatus, and delaying said triggering of the flash of light from said light source and capturing the image on said digital image sensor, until said motion has stopped.

13. The apparatus of any preceding embodiment, wherein said motion is detected by a motion detection device selected from a group of motion detection devices consisting of accelerometers, inertial sensors, gyroscopes, pose sensors, and compasses.

14. The apparatus of any preceding embodiment, wherein said instructions configured for execution on the processor, further comprises localizing, monitoring, and tracking exact landmarks and pathology of the eye including selected from the group of ocular features consisting of nevi, neovascularization, and retinal drusen or hemorrhage known from either a previous or a current examination.

15. The apparatus of any preceding embodiment, wherein said instructions configured for execution on the processor, further comprises providing relative location information for structures within the eye which have been previously imaged, to assist in imaging those areas and in stitching of collected retinal images.

16. The apparatus of any preceding embodiment, wherein said instructions configured for execution on the processor, further comprises compiling a retinal map for the eye of this subject in relation to the displayed fixation target, whereby specific retinal areas may be readily found when further imaging is to be performed.

17. A portable retinal imaging apparatus for fundus imaging of an eye, said apparatus comprising: (a) a housing; (b) a retention structure on said housing for retaining a mobile device configured with a digital image sensor and display and a computer processor and programming for capturing digital images for output on said display and/or storing in a memory; (c) a light source in said housing configured for directing light along an illumination path of said retinal imaging apparatus; (d) an optical system configured for collecting light from a pupil of a subject eye being imaged and directing that light along an imaging path toward the digital image sensor of the mobile device; (e) a light splitter forming a junction between said illumination path and said imaging path, wherein illumination from said light source is directed along said illumination path to said light splitter which redirects illumination into said imaging path into a posterior region of the subject eye being imaged; (f) a fixation display configured for displaying a fixation target for directing the eye of the subject which is being imaged; (g) a computer processor coupled to said light source and said digital image sensor; and (h) a non-transitory memory storing instructions executable by the processor; (j) wherein said instructions, when executed by the processor, perform steps comprising: (j)(i) outputting said fixation target from said fixation display so that light is collected along said imaging path from a first retinal area of the eye; (j)(ii) triggering a flash of light from said light source in synchrony with capturing a retinal image on the digital image sensor of the mobile device; (j)(iii) outputting said fixation target from said fixation display so that light is collected along said imaging path from another retinal area of the eye; (j)(iv) triggering a flash of light from said light source in synchrony with capturing an image on the digital image sensor of the mobile device from this other retinal area of the eye; and (j)(v) repeating steps (j)(iii)-(j)(iv) to capture multiple retinal areas of the eye which can be stitched together into a composite image having a field of view wider than the image captured on said digital image sensor.

18. A portable retinal imaging apparatus for fundus imaging of an eye, said apparatus comprising: (a) a housing; (b) a retention structure on said housing for retaining a mobile device configured with a digital image sensor and display and a computer processor and programming for capturing digital images for output on said display and/or storing in a memory; (c) a light source in said housing configured for directing light along an illumination path of said retinal imaging apparatus; (d) wherein said light source is configured for outputting both high intensity lighting when capturing images, and low intensity lighting in the far red wavelength spectrum of visible light for previewing retinal image locations; (e) an optical system configured for collecting light from a pupil of a subject eye being imaged and directing that light along an imaging path toward the digital image sensor of the mobile device; (f) a light splitter forming a junction between said illumination path and said imaging path, wherein illumination from said light source is directed along said illumination path to said light splitter which redirects illumination into said imaging path into a posterior region of the subject eye being imaged; (g) a fixation display configured for displaying a fixation target for directing the eye of the subject which is being imaged; (h) a computer processor coupled to said light source and said digital image sensor; and (j) a non-transitory memory storing instructions executable by the processor; (k) wherein said instructions, when executed by the processor, perform steps comprising: (k)(i) entering a preview mode in which said secondary light source is activated and light is collected along said imaging path for receipt by the mobile device which displays still or video images of the eye, as the fixation target is moved in response to user input on said mobile device which communicates with said apparatus until a desired portion of the retina is positioned along said imaging path; (k)(ii) triggering a flash of light from said light source in synchrony with capturing a retinal image on the digital image sensor of the mobile device; (k)(iii) entering preview mode and outputting said fixation target from said fixation display so that light is collected along said imaging path from another retinal area of the eye; (k)(iv) triggering a flash of light from said light source in synchrony with capturing an image on the digital image sensor of the mobile device from this other retinal area of the eye; and (k)(v) repeating steps (k)(iii)-(k)(iv) to capture multiple retinal areas of the eye which can be stitched together into a composite image having a field of view wider than the image captured on said digital image sensor.

19. The apparatus of any preceding embodiment, wherein said instructions configured for execution on the processor, further comprises detecting a motion of the apparatus, and delaying said triggering of the flash of light from said light source and capturing the image on said digital image sensor, until said motion has stopped.

20. The apparatus as recited in claim 18, wherein said instructions configured for execution on the processor, further comprises localizing, monitoring, and tracking exact landmarks and pathology of the eye including selected from the group of ocular features consisting of nevi, neovascularization, and retinal drusen or hemorrhage known from either a previous or a current examination.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A portable retinal imaging apparatus for fundus imaging of an eye, said apparatus comprising:
   (a) a light source configured for directing light along an illumination path of said retinal imaging apparatus;
   (b) an optical system configured for collecting light from a pupil of a subject eye being imaged and directing that light along an imaging path onto a digital image sensor configured for capturing an image;
   (c) a light splitter forming a junction between said illumination path and said imaging path, wherein illumination from said light source is directed along said illumination path to said light splitter which redirects illumination into said imaging path into a posterior region of the subject eye being imaged;
   (d) a fixation display configured for displaying a fixation target for directing the eye of the subject which is being imaged;
   (e) a processor coupled to said light source and said digital image sensor; and
   (f) a non-transitory memory storing instructions executable by the processor;
   (g) wherein said instructions, when executed by the processor, perform steps comprising:
      (i) outputting said fixation target from said fixation display so that light is collected along said imaging path from a first retinal area of the eye;
      (ii) triggering a flash of light from said light source in synchrony with capturing a retinal image on said digital image sensor; and
      (iii) localizing, monitoring, and tracking exact landmarks and pathology of the eye including selected from the group of ocular features consisting of nevi, neovascularization, and retinal drusen or hemorrhage known from either a previous or a current examination.

2. The apparatus as recited in claim 1, wherein said instructions configured for executed by the processor after step (g)(ii) in claim 1, further comprises:
   (a) outputting said fixation target from said fixation display so that light is collected along said imaging path from another retinal area of the eye;
   (b) triggering a flash of light from said light source in synchrony with capturing an image on said digital image sensor from this other retinal area of the eye; and
   (c) repeating steps (a)-(b) to capture multiple retinal areas of the eye which can be stitched together into a composite image having a field of view wider than the image captured on said digital image sensor.

3. The apparatus as recited in claim 1, wherein said light source is further configured with a secondary source of light for use during a preview mode.

4. The apparatus as recited in claim 3, wherein said instructions configured for executed by the processor, further comprises:
   (a) entering a preview mode in which said secondary light source is activated;
   (b) collecting light along said imaging path for receipt by said digital image sensor;
   (c) displaying still or video images of the eye as received by said digital image sensor; and
   (d) changing said fixation target to move the eye of the subject until a desired portion of the retina is positioned along said imaging path, prior to triggering a flash of light from said light source in synchrony with capturing a retinal image on said digital image sensor.

5. The apparatus as recited in claim 3, wherein said secondary source of light is generated at a sufficiently low intensity and/or of a wavelength which is sufficiently separate from a visible spectrum of the eye, to prevent changing the imaging conditions of the eye.

6. The apparatus as recited in claim 3, wherein said secondary source of light comprises a low intensity light source at a far red portion of the light spectrum to which the eye is sensitive.

7. The apparatus as recited in claim 1, wherein said fixation display is visible to another eye of the subject which is not being imaged on said digital image sensor.

8. The apparatus as recited in claim 1, wherein said apparatus is configured for either manual or automatic location adjustment of said fixation target to bring desired retina regions of eye into view on said digital image sensor.

9. The apparatus as recited in claim 1, wherein said apparatus is configured for being mechanically and optically coupled to a mobile electronic device containing a digital image sensor and configured for executing application programming for capturing retinal images on said digital image sensor.

10. The apparatus as recited in claim 9, wherein said apparatus is configured for being controlled in response to communications from the mobile electronic device.

11. The apparatus as recited in claim 10, wherein said apparatus is configured for changing the fixation target, and lighting output in response to swipe gestures and taps on the display screen of said mobile electronic device.

12. The apparatus as recited in claim 1, wherein said instructions configured for execution on the processor, further comprises detecting a motion of the apparatus, and delaying said triggering of the flash of light from said light source and capturing the image on said digital image sensor, until said motion has stopped.

13. The apparatus as recited in claim 1, wherein said motion is detected by a motion detection device selected from a group of motion detection devices consisting of accelerometers, inertial sensors, gyroscopes, pose sensors, and compasses.

14. A portable retinal imaging apparatus for fundus imaging of an eye, said apparatus comprising:
   (a) a housing;
   (b) a retention structure on said housing for retaining a mobile device configured with a digital image sensor and display and a computer processor and programming for capturing digital images for output on said display and/or storing in a memory;
   (c) a light source in said housing configured for directing light along an illumination path of said retinal imaging apparatus;
   (d) an optical system configured for collecting light from a pupil of a subject eye being imaged and directing that light along an imaging path toward the digital image sensor of the mobile device;
   (e) a light splitter forming a junction between said illumination path and said imaging path, wherein illumination from said light source is directed along said illumination path to said light splitter which redirects illumination into said imaging path into a posterior region of the subject eye being imaged;
   (f) a fixation display configured for displaying a fixation target for directing the eye of the subject which is being imaged;
   (g) a computer processor coupled to said light source and said digital image sensor; and
   (h) a non-transitory memory storing instructions executable by the processor;
   (j) wherein said instructions, when executed by the processor, perform steps comprising:
      (i) outputting said fixation target from said fixation display so that light is collected along said imaging path from a first retinal area of the eye;
      (ii) triggering a flash of light from said light source in synchrony with capturing a retinal image on the digital image sensor of the mobile device;
      (iii) outputting said fixation target from said fixation display so that light is collected along said imaging path from another retinal area of the eye;
      (iv) triggering a flash of light from said light source in synchrony with capturing an image on the digital image sensor of the mobile device from this other retinal area of the eye; and
      (v) repeating steps (j)(iii)-(j)(iv) to capture multiple retinal areas of the eye which can be stitched together into a composite image having a field of view wider than the image captured on said digital image sensor.

15. A portable retinal imaging apparatus for fundus imaging of an eye, said apparatus comprising:
   (a) a housing;
   (b) a retention structure on said housing for retaining a mobile device configured with a digital image sensor and display and a computer processor and programming for capturing digital images for output on said display and/or storing in a memory;
   (c) a light source in said housing configured for directing light along an illumination path of said retinal imaging apparatus;
   (d) wherein said light source is configured for outputting both high intensity lighting when capturing images, and low intensity lighting in the far red wavelength spectrum of visible light for previewing retinal image locations;
   (e) an optical system configured for collecting light from a pupil of a subject eye being imaged and directing that light along an imaging path toward the digital image sensor of the mobile device;
   (f) a light splitter forming a junction between said illumination path and said imaging path, wherein illumination from said light source is directed along said illumination path to said light splitter which redirects illumination into said imaging path into a posterior region of the subject eye being imaged;
   (g) a fixation display configured for displaying a fixation target for directing the eye of the subject which is being imaged;
   (h) a computer processor coupled to said light source and said digital image sensor; and
   (j) a non-transitory memory storing instructions executable by the processor;
   (k) wherein said instructions, when executed by the processor, perform steps comprising:
      (i) entering a preview mode in which said secondary light source is activated and light is collected along said imaging path for receipt by the mobile device which displays still or video images of the eye, as the fixation target is moved in response to user input on said mobile device which communicates with said apparatus until a desired portion of the retina is positioned along said imaging path
      (ii) triggering a flash of light from said light source in synchrony with capturing a retinal image on the digital image sensor of the mobile device;
      (iii) entering preview mode and outputting said fixation target from said fixation display so that light is collected along said imaging path from another retinal area of the eye;
      (iv) triggering a flash of light from said light source in synchrony with capturing an image on the digital image sensor of the mobile device from this other retinal area of the eye; and
      (v) repeating steps (k)(iii)-(k)(iv) to capture multiple retinal areas of the eye which can be stitched together into a composite image having a field of view wider than the image captured on said digital image sensor.

16. The apparatus as recited in claim 15, wherein said instructions configured for execution on the processor, further comprises detecting a motion of the apparatus, and delaying said triggering of the flash of light from said light source and capturing the image on said digital image sensor, until said motion has stopped.

17. The apparatus as recited in claim 15, wherein said instructions configured for execution on the processor, further comprises localizing, monitoring, and tracking exact landmarks and pathology of the eye including selected from the group of ocular features consisting of nevi, neovascularization, and retinal drusen or hemorrhage known from either a previous or a current examination.

18. A portable retinal imaging apparatus for fundus imaging of an eye, said apparatus comprising:
(a) a light source configured for directing light along an illumination path of said retinal imaging apparatus;
(b) an optical system configured for collecting light from a pupil of a subject eye being imaged and directing that light along an imaging path onto a digital image sensor configured for capturing an image;
(c) a light splitter forming a junction between said illumination path and said imaging path, wherein illumination from said light source is directed along said illumination path to said light splitter which redirects illumination into said imaging path into a posterior region of the subject eye being imaged;
(d) a fixation display configured for displaying a fixation target for directing the eye of the subject which is being imaged;
(e) a processor coupled to said light source and said digital image sensor; and
(f) a non-transitory memory storing instructions executable by the processor;
(g) wherein said instructions, when executed by the processor, perform steps comprising:
(i) outputting said fixation target from said fixation display so that light is collected along said imaging path from a first retinal area of the eye;
(ii) triggering a flash of light from said light source in synchrony with capturing a retinal image on said digital image sensor; and
(iii) providing relative location information for structures within the eye which have been previously imaged, to assist in imaging those areas and in stitching of collected retinal images.

19. The apparatus as recited in claim 18, wherein said instructions configured for executed by the processor after step (g)(ii) in claim 1, further comprises:
(a) outputting said fixation target from said fixation display so that light is collected along said imaging path from another retinal area of the eye;
(b) triggering a flash of light from said light source in synchrony with capturing an image on said digital image sensor from this other retinal area of the eye; and
(c) repeating steps (a)-(b) to capture multiple retinal areas of the eye which can be stitched together into a composite image having a field of view wider than the image captured on said digital image sensor.

20. The apparatus as recited in claim 18, wherein said light source is further configured with a secondary source of light for use during a preview mode.

21. The apparatus as recited in claim 20, wherein said instructions configured for executed by the processor, further comprises:
(a) entering a preview mode in which said secondary light source is activated;
(b) collecting light along said imaging path for receipt by said digital image sensor;
(c) displaying still or video images of the eye as received by said digital image sensor; and
(d) changing said fixation target to move the eye of the subject until a desired portion of the retina is positioned along said imaging path, prior to triggering a flash of light from said light source in synchrony with capturing a retinal image on said digital image sensor.

22. The apparatus as recited in claim 20, wherein said secondary source of light is generated at a sufficiently low intensity and/or of a wavelength which is sufficiently separate from a visible spectrum of the eye, to prevent changing the imaging conditions of the eye.

23. The apparatus as recited in claim 20, wherein said secondary source of light comprises a low intensity light source at a far red portion of the light spectrum to which the eye is sensitive.

24. The apparatus as recited in claim 18, wherein said fixation display is visible to another eye of the subject which is not being imaged on said digital image sensor.

25. The apparatus as recited in claim 18, wherein said apparatus is configured for either manual or automatic location adjustment of said fixation target to bring desired retina regions of eye into view on said digital image sensor.

26. The apparatus as recited in claim 18, wherein said apparatus is configured for being mechanically and optically coupled to a mobile electronic device containing a digital image sensor and configured for executing application programming for capturing retinal images on said digital image sensor.

27. The apparatus as recited in claim 26, wherein said apparatus is configured for being controlled in response to communications from the mobile electronic device.

28. The apparatus as recited in claim 27, wherein said apparatus is configured for changing the fixation target, and lighting output in response to swipe gestures and taps on the display screen of said mobile electronic device.

29. The apparatus as recited in claim 18, wherein said instructions configured for execution on the processor, further comprises detecting a motion of the apparatus, and delaying said triggering of the flash of light from said light source and capturing the image on said digital image sensor, until said motion has stopped.

30. The apparatus as recited in claim 18, wherein said motion is detected by a motion detection device selected from a group of motion detection devices consisting of accelerometers, inertial sensors, gyroscopes, pose sensors, and compasses.

31. A portable retinal imaging apparatus for fundus imaging of an eye, said apparatus comprising:
(a) a light source configured for directing light along an illumination path of said retinal imaging apparatus;
(b) an optical system configured for collecting light from a pupil of a subject eye being imaged and directing that light along an imaging path onto a digital image sensor configured for capturing an image;
(c) a light splitter forming a junction between said illumination path and said imaging path, wherein illumination from said light source is directed along said illumination path to said light splitter which redirects illumination into said imaging path into a posterior region of the subject eye being imaged;
(d) a fixation display configured for displaying a fixation target for directing the eye of the subject which is being imaged;
(e) a processor coupled to said light source and said digital image sensor; and
(f) a non-transitory memory storing instructions executable by the processor;
(g) wherein said instructions, when executed by the processor, perform steps comprising:
(i) outputting said fixation target from said fixation display so that light is collected along said imaging path from a first retinal area of the eye;
(ii) triggering a flash of light from said light source in synchrony with capturing a retinal image on said digital image sensor; and (iii) compiling a retinal map for the eye of this subject in relation to the displayed fixation target, whereby specific retinal areas may be readily found when further imaging is to be performed.

32. The apparatus as recited in claim 31, wherein said instructions configured for executed by the processor after step (g)(ii) in claim 1, further comprises:
(a) outputting said fixation target from said fixation display so that light is collected along said imaging path from another retinal area of the eye;
(b) triggering a flash of light from said light source in synchrony with capturing an image on said digital image sensor from this other retinal area of the eye; and
(c) repeating steps (a)-(b) to capture multiple retinal areas of the eye which can be stitched together into a composite image having a field of view wider than the image captured on said digital image sensor.

33. The apparatus as recited in claim 31, wherein said light source is further configured with a secondary source of light for use during a preview mode.

34. The apparatus as recited in claim 33, wherein said instructions configured for executed by the processor, further comprises:
(a) entering a preview mode in which said secondary light source is activated;
(b) collecting light along said imaging path for receipt by said digital image sensor;
(c) displaying still or video images of the eye as received by said digital image sensor; and
(d) changing said fixation target to move the eye of the subject until a desired portion of the retina is positioned along said imaging path, prior to triggering a flash of light from said light source in synchrony with capturing a retinal image on said digital image sensor.

35. The apparatus as recited in claim 34, wherein said secondary source of light is generated at a sufficiently low intensity and/or of a wavelength which is sufficiently separate from a visible spectrum of the eye, to prevent changing the imaging conditions of the eye.

36. The apparatus as recited in claim 34, wherein said secondary source of light comprises a low intensity light source at a far red portion of the light spectrum to which the eye is sensitive.

37. The apparatus as recited in claim 31, wherein said fixation display is visible to another eye of the subject which is not being imaged on said digital image sensor.

38. The apparatus as recited in claim 31, wherein said apparatus is configured for either manual or automatic location adjustment of said fixation target to bring desired retina regions of eye into view on said digital image sensor.

39. The apparatus as recited in claim 31, wherein said apparatus is configured for being mechanically and optically coupled to a mobile electronic device containing a digital image sensor and configured for executing application programming for capturing retinal images on said digital image sensor.

40. The apparatus as recited in claim 39, wherein said apparatus is configured for being controlled in response to communications from the mobile electronic device.

41. The apparatus as recited in claim 40, wherein said apparatus is configured for changing the fixation target, and lighting output in response to swipe gestures and taps on the display screen of said mobile electronic device.

42. The apparatus as recited in claim 31, wherein said instructions configured for execution on the processor, further comprises detecting a motion of the apparatus, and delaying said triggering of the flash of light from said light source and capturing the image on said digital image sensor, until said motion has stopped.

43. The apparatus as recited in claim 31, wherein said motion is detected by a motion detection device selected from a group of motion detection devices consisting of accelerometers, inertial sensors, gyroscopes, pose sensors, and compasses.

* * * * *